(12) United States Patent
Kim et al.

(10) Patent No.: US 6,841,661 B2
(45) Date of Patent: Jan. 11, 2005

(54) GLYCOPEPTIDE ANTIBACTERIAL COMPOUNDS, COMPOSITIONS CONTAINING SAME AND METHODS OF USING SAME

(75) Inventors: Ronald M. Kim, Hoboken, NJ (US); Daniel E. Kahne, Princeton, NJ (US); Kevin T. Chapman, Scotch Plains, NJ (US)

(73) Assignee: Princeton Univerisity, Princeton, NJ (US)

( * ) Notice: Subject to any disclaimer, the term of this patent is extended or adjusted under 35 U.S.C. 154(b) by 0 days.

(21) Appl. No.: 10/262,858

(22) Filed: Oct. 3, 2002

(65) Prior Publication Data

US 2003/0224975 A1 Dec. 4, 2003

Related U.S. Application Data

(63) Continuation of application No. 09/574,225, filed on May 19, 2000, now Pat. No. 6,498,238.
(60) Provisional application No. 60/134,841, filed on May 19, 1999.

(51) Int. Cl.[7] .............................................. C07G 11/00
(52) U.S. Cl. .............................. 536/16.8; 514/1; 514/8; 514/23
(58) Field of Search ........................ 536/16.8; 514/1, 514/8, 23

(56) References Cited

U.S. PATENT DOCUMENTS 6,498,238 B1 * 12/2002 Kim et al. ................. 536/16.8

FOREIGN PATENT DOCUMENTS

| EP | 0802199 A2 | 10/1997 |
| EP | 0881229 A2 | 12/1998 |
| WO | WO 00/04044 | 1/2000 |
| WO | WO 00/42067 | 7/2000 |

OTHER PUBLICATIONS

PCT Notification of Transmittal of The International Search Report or the Declaration dated Oct. 10, 2000.
"In Vivo Activity and Pharmacokinetic Evaluation of a Novel Long–Acting Carbaapenem Antibiotic, MK–826 (L–749,345)", Charles J. Gill et al, Antimicrobial Agents and Chemotherapy, Aug. 1998, vol. 42, No. 8, pp. 1996–2001.
"The Use of the Angular Transformation in Biological Assays*", Lila F. Knudsen et al, American Statistical Association, pp. 282–296.
"Antibacterial Activities and Modes of Actiioon of Vancomycin and Related Glycopeptides", R. Nagarajan, Antimicrobial Agents and Chemotherapy, Apr. 1991, pp. 605–609.
"Selective Cleavage of Vancosamine, Glucose, and N–Methyl–leucine from Vancomycin and Related Antibiotics", R. Nagaarajan et al, J. Chem. Soc., Chem. Commun., 1988, pp. 1306–1307.
"Structural Modifications of Glycopeptide Antibiotics", Adriano Malabarba et al, Medical Research Reviews, 1997, vol. 17, No. 1, pp. 69–137.
"Synthesis and Biological Activity of Derivatives of Glycopeptide Antibiotics Eremomycin and Vancomycin Nitrosated, Acylated or Carbamoyloated at the N–Terminal", A. Y. Pavlov et al, Journal of Antibiotics, Nov. 1993, vol. 46, No. 11, pp. 1731–1739.

* cited by examiner

*Primary Examiner*—Jezia Riley
(74) *Attorney, Agent, or Firm*—McDermott Will & Emery LLP

(57) ABSTRACT

The present invention relates to vancomycin analogs in which the vancosamine residue is substituted with a lipid-like substituent that includes a first aryl moiety and a second aryl moiety joined together by a flexible linker moiety, that is not a single bond directly joining the first aryl moiety and the second aryl moiety, and a glucose C-6 substituent modified to be other than the naturally occurring hydroxyl group, or pharmaceutically acceptable salts thereof.

19 Claims, No Drawings

GLYCOPEPTIDE ANTIBACTERIAL COMPOUNDS, COMPOSITIONS CONTAINING SAME AND METHODS OF USING SAME

CROSS-REFERENCE TO RELATED APPLICATION

This application is a continuation of Ser. No. 09/574,225 filed May 19, 2000 now U.S. Pat. No. 6,498,238 which claims the benefit of the filing date of Provisional Application Ser. No. 60/134,841, filed May 19, 1999, under 35 USC 119.

FIELD OF THE INVENTION

The present invention relates to novel derivatives of natural products, methods for their preparation, and the determination of their activity. In particular, the present invention relates to novel derivatives of glycopeptide antibiotics, such as vancomycin, methods for their preparation and their uses for the treatment of bacterial infection.

In the preferred embodiment, the present invention relates to vancomycin-derived glycopeptide antibacterial agents, which are characterized by a heptapeptide structure that is covalently linked to at least one saccharide group. The saccharide group(s) can be substituted with various substituent groups as described herein.

BACKGROUND OF THE INVENTION

An example of a known glycopeptide antibiotic is vancomycin, which contains a disaccharide substituent linked to a heptapeptide structure. See Malabarba A., et al., Med. Res. Rev., 17(1):69–137 (1997a); Nagarajan R. et al., J. Chem. Soc. Chem. Comm. 1306–1307(1988); Nagarajan R., Antimicr. Agents Chemother., 35:605–609 (1991); and Nagaranjan R., J. Antibiotics, 46:1181–1195 (1993). Vancomycin is effective against gram positive bacteria. However, vancomycin resistant strains have been recently observed, thus increasing the need for new and effective therapeutic agents.

The glycopeptides of the present invention are useful against many gram positive microorganisms, including vacomycin resistant enterococcus (VRE), methicillin resistant Staphylococcus aureus (MRSA), methicillin resistant Staphylococcus epidermidis (MRSE), and methicillin resistant coagulase negative Staphylococci (MRCNS). The antibacterial compounds of the present invention thus comprise an important new contribution to the development of therapeutic regimens for treating infections caused by these difficult to control pathogens and resistant strains.

There is an increasing need for agents effective against such pathogens, which are at the same time relatively free from undesirable side effects. Moreover, the physicochemical and pharmacological characteristics of candidate drugs, including their solubility, charge, hygroscopic characteristics, lipophilicity, bioavailability, tissue distribution, serum half-life and the like can play important roles in determining the success or failure of a candidate drug in the clinic. For example, it has been reported that a vancomycin analog in the Phase III clinical studies, which bears a chlorophenylbenzyl (also referred elsewhere in this application as chlorobiphenyl; other substituents are described in, e.g., Rodriguez, M. J., J. Antibiotics, 51(6):560–569 (1998)) substituent on the amine nitrogen of vancosamine and a free hydroxyl group on the C-6 position of glucose, exhibits a serum half-life in excess of two weeks. It has also been reported that traces of this vancomycin analog can be detected in patients up to a year after drug administration. Clearly, should a patient experience any adverse reaction to any drug, it would be beneficial if the patient's body could metabolize and/or clear the drug relatively quickly, e.g., within about 24 or less, preferably within about 12 hours or less, most preferably within about 6–8 hours or less.

It should be noted that antibiotics of the type that include vancomycin are typically administered parenterally, that is intravenously. Hence, a relatively high clearance rate would not typically be a disadvantage, and as stated above, would be of potential great benefit to certain patients. Such intravenous formulations impose certain requirements on a drug, not the least of which is adequate solubility in the formulation medium. Thus, poorly soluble drugs may be unsuitable as a practical matter because the clinician is unable to dissolve the drug in a formulation, much less deliver adequate amounts of the drug via intravenous drip. Generally, the pH of the formulation is buffered to correspond to physiological pH, which is about 7.4. While some leeway is possible in the pH of an intravenous formulation, pain at the site of injection typically limits the useful range of pH to no less than about 5 to no greater than about 8. Preferably, the pH of an intravenous formulation ranges from about 6–8, more preferably from about 7–8 and most preferably at or about physiological pH (e.g., about 7.2–7.6).

Hence, there has been an on-going search for compounds that exhibit not only increased potency against resistant strains but also the physicochemical and pharmacological characteristics that enhance the effectiveness of a candidate compound and which may determine ultimately its acceptance in the clinic and resulting commercial success.

SUMMARY OF THE INVENTION

The present invention provides new analogs of vancomycin, which exhibit enhanced biological activity and improved physicochemical and pharmacological characteristics. The overall properties of these analogs exhibit substantial potential as drug candidates for treating infections caused by certain pathogens, including various strains of drug resistant bacteria. Accordingly, a general method is provided for the preparation of such compounds, along with methods of using them for the treatment of vertebrate conditions, including those afflicting mammals and especially those suffered by humans. Such conditions typically, although not exclusively, involve infections and other pathological conditions caused by bacteria and other microorganisms.

In particular, it has been observed that certain substituents positioned at the amine nitrogen of vancosamine and at the C-6 position of the glucose of vancomycin provide enhanced biological activity according to in vitro and in vivo assays and give rise to desirable physicochemical and pharmacological characteristics, all of which improve a candidate drug's chances of success beyond the lab bench and in the clinic. More particularly, the present invention provides for lipid-like substituents on the amine nitrogen of vancosamine, which include at least two aryl moieties that are joined (i.e., covalently bound) together with a flexible linker moiety. By "lipid-like" substituent is meant a "lipophilic" substituent which refers to the tendency of the compound or substituent thereon to lack an affinity for, to repel or to fail to absorb water, or to be immiscible in water. The term "lipophilic" is not meant to exclude compounds or substituents thereon that are not completely immiscible in water. By "flexible linker" is meant that the linker or linking groups provides at least some degree of flexible movement in the substituent containing the lipid-like substituent. The flexible linker moiety joining the two aryl moieties of the lipid-like substituent on the vancosamine nitrogen is not a single bond directly joining the two aryl moieties. The flexible linker moiety appears to increase the lipophilicity of the molecule, as a whole, while potentially providing a site of attack for the metabolic and/or clearance processes of the body.

While a wide range of flexible linker moieties are potentially useful in the present invention, such as alkylene groups, alkylene ethers, alkylene thioethers, ethers, thioethers, acyls, sulfonyls, sulfoxides, alkylene amines, unsaturated aliphatic groups and the like, the preferred embodiments are those that (together with at least the first or second aryl moiety and possibly other functional groups present in the substituent) give rise to benzyl, benzylamino, benzyloxy, benzylthioether groups, phenyl ketones, or combinations thereof. Doubtless, one of ordinary skill in the art could contemplate other flexible linker moieties, which could give rise to increased lipophilicity and increased likelihood of breakdown/clearance by the body. The same or a different flexible linker moiety is also present to join the amine nitrogen of vancosamine to the first aryl moiety part of the lipid-like substituent. In a preferred embodiment of the invention, the lipid-like substituent comprises the formula K—Ar$_1$—Z—Ar$_2$, as defined further below but which generally includes first and second aryl moieties, Ar$_1$ and Ar$_2$, and flexible linker moieties K and Z, provided that Z is not a single bond directly joining Ar1 and Ar$_2$ It has been observed that of the wide range of possible substituents that can be positioned at the glucose C-6 position of vancomycin, polar substituents (that is, substituents that bear a charge or possess the capacity to bear a charge, either positive or negative, at some useful range of pH, but preferably at or about physiological pH) enhance biological activity and/or provide advantageous physicochemical and/or pharmacological characteristics. The term "polar" as used herein to describe a compound of the present invention or a substituent thereon, refers to the tendency of the compound or substituent thereon to have an affinity for, to attract or to absorb water, or to be miscible in water. The term "polar" is not meant to exclude compounds or substituents thereon that are not completely miscible in water. Most preferably, the polar substituent is part of an N-substituent (that is, an amine or amine based substituent) at the C-6 position, including but not limited to a free amine, substituted amines, alpha-amino acid amides, carboxylic acid amides (e.g., the carboxylic acid amide obtained from the reaction of a C-6 amine with for example succinic acid, other diacids, anhydrides, or other bifunctional acids), quaternary ammonium salts and the like. In particular, when not a free amine at the glucose C-6 position, the invention contemplates those substituents that can be joined to the amine group at the C-6 position of glucose and which (i) introduces a wide variety of functional groups, as part of or which can be added to the substituent, and (ii) also provides for one or more primary or secondary amine sites at a distal position (that is, a position in the substituent which is removed from the C-6 amine by two or more carbon atoms or in which the amine site is separated from the C-6 amine by three or more chemical bonds). Still in other embodiments of the invention, the polar substituent possesses polar groups, such as C(O), C(S), Nh$_2$. NHR$_2$ groups and the like and combinations thereof, which may not ordinarily be charged. An example of such a polar substituent is urea or thiourea. It should be understood that the polar substituent contemplated by the present invention does not include the naturally occurring substituent at glucose C-6 of vancomycin, which is a hydroxyl group.

The preferred vancomycin compounds of the invention, including their pharmaceutically acceptable salts, are represented by the general Formula 1, presented below:

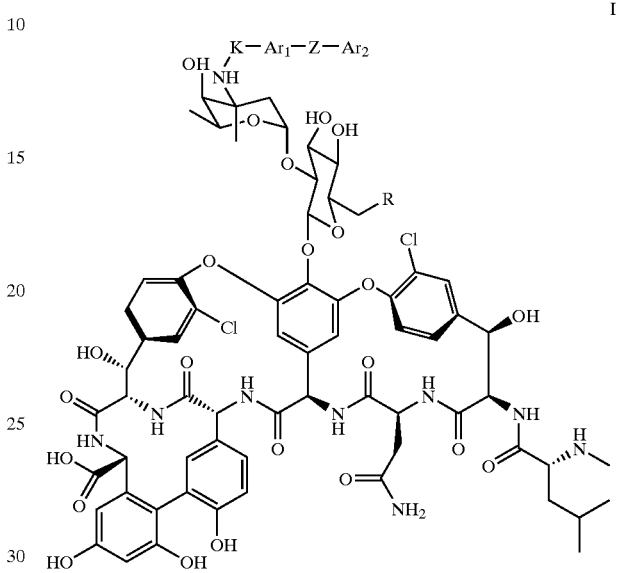

I in which R represents a polar substituent and K—Ar$_1$—Z—Ar$_2$ represents a lipid-like substituent, as described above.

The invention is also directed to pharmaceutical compositions, including enteral and parenteral formulations of the compounds disclosed herein. Also disclosed are methods of determining the biological activities of the various compounds of interest to the invention, as well as those of lesser interest. Methods of preparing the compounds and of utilizing same in a treatment regimen are also described and contemplated.

A more detailed description of the preferred embodiments of the invention follows for the benefit of the reader. Additional objects of the invention will become apparent to the reader after consideration of the entire disclosure.

DETAILED DESCRIPTION OF THE INVENTION

As stated above, it has been observed that certain vancomycin analogs bearing vancosamine lipid-like substituents of the formula K—Ar$_1$—Z—Ar$_2$ possess enhanced biological activity relative to those conventional substituents that do not fall within the scope of the formula. These vancomycin analogs consistently exhibit at least a two- to four-fold increase in activity over those vancomycin analogs bearing substituents known in the art, especially in those bacterial strains that exhibit the greatest resistance to vancomycin or teicoplanin. These strains include CL 4931, CL 5053, CL 5242 and CL 4877. See, Example 5.8, Table 3 and Table 4, below. Moreover, it is anticipated that improved physicochemical and pharmacological properties of the vancomycin analogs of the invention, including at least improved solubility characteristics and greater clearance rates, will contribute to a higher likelihood of success for these compounds in the clinic.

Broadly speaking, the constituents of the lipid-like substituent, K—Ar$_1$—Z—Ar$_2$, can be the following:

K and Z can be the same or different and selected from any linking group which will provide the characteristics of flexibility required for the flexible linker. Especially preferred groups of this type comprise carbonyl, sulfonyl, (C$_{1-6}$)alkylene, (C$_{1-6}$)alkyleneoxy, oxy(C$_{1-6}$)alkylene, (C$_{1-6}$)alkyleneamino, amino(C$_{1-6}$)alkylene, (C$_{1-3}$)alkyleneoxy-(C$_{1-3}$)alkylene, (C$_{1-6}$)alkylenethio, thio(C$_{1-6}$)alkylene, (C$_{1-6}$)alkylenecarbonyl, aminocarbonyl or carbonylamino, (C$_{1-6}$)alkyleneaminocarbonyl, aminocarbonyl(C$_{1-6}$)alkylene, oxy, oxycarbonyl or carbonyloxy, (C$_{1-6}$)alkyleneoxycarbonyl, oxycarbonyl(C$_{1-6}$)alkylene, aminosulfonyl, or sulfonylamino, Ar$_1$ and Ar$_2$ can be the same or different and selected from aromatic or heterocyclic groups, each optionally monosubstituted, disubstituted, or trisubstituted with R$_1$; wherein R$_1$ can be halo; R$_2$; CN; NO$_2$; CF$_3$; OCH$_x$F$_{(3-x)(x=0-3)}$; NHSO$_2$R$_2$; OR$_2$; SR$_2$; N(R$_2$)$_2$; N$^+$ (R$_2$)3; C(O)N(R$_2$)$_2$; SO$_2$N(R$_2$)$_2$; heterocyclic; CO$_2$R$_2$; OC(O)R$_2$; NR$_2$C(O)R$_2$; or NHC(O)R$_2$; and wherein R$_2$ independently (where more than one R$_2$ is present) represents H, aryl, straight or branched (C$_{14}$) alkyl, arylalkyl, heterocyclic, heterocyclic (C$_1$–C$_6$) alkyl, aroyl, alkanoyl, alkanoyloxy, alkanoylamido, alkylsulfonyl, arylsulfonyl; and when two R$_2$ groups are present, they may optionally be linked by one or more covalent bonds to form one or more rings, which may be aromatic, aliphatic, or heterocyclic.

In a preferred embodiment of the invention, the polar substituent, R, has the formula:

in which the groups R$_3$ and R$_4$ may independently be present or absent and, if present, may be the same or different and selected from H, alkyl, aryl, heterocyclic, aralkyl, heterocyclicalkyl, alkylcarbonyl, arylcarbonyl, heterocycliccarbonyl, aminocarbonyl, substituted arninocarbonyl, substituted oxycarbonyl, alkylsulfonyl, arylsulfonyl, heterocyclicsulfonyl, aminosulfonyl, substituted aminosulfonyl, amidino, or substituted amidino, said alkyl, aryl, heterocyclic, arylalkyl, heterocyclicalkyl, alkylcarbonyl, arylcarbonyl, or heterocycliccarbonyl being optionally substituted with 1–3 groups of R$_1$; and wherein R$_3$ and R$_4$ may be linked to one another or to one or both of the others by one or more covalent bonds to form one or more aryl or heterocyclic rings of 3–20 members, optionally comprised of C, N, 0, or S. Preferably R is Nh$_2$ or substituted Nh$_2$.

Examples of preferred polar substituent groups are provided in the Tables and the Chart included in this disclosure, which also provide examples of preferred lipid-like substituents having two or more flexible linkers.

The term "alkyl" refers to a monovalent alkane (hydrocarbon) derived radical comprising 1 to about 20 carbon atoms connected by single or multiple bonds, unless otherwise indicated. The alkyl group may be straight, branched, or cyclic. Examples of alkyl groups include, but are not limited to, methyl, ethyl, propyl, isopropyl, butyl, secbutyl, t-butyl, pentyl, cyclopentyl, hexyl and cyclohexyl. The term "alkylene" refers to a hydrocarbon radical comprising I to about 20 carbon atoms connected by single or multiple bonds, unless otherwise indicated, and which is bound to other ftunctional or chemical groups of the molecule at least at two sites. Examples of alkylene groups include, but are not limited to, —CH$_2$—, —CH$_2$CH$_2$——CH$_2$CH$_2$CH$_2$——CH$_2$ (CH$_3$)CH$_2$—, and like, wherein each dash represents a point of attachment to another chemical or functional group of the molecule. When substituted, alkyl and alkylene groups may be substituted with up to three substituent groups, selected from Ra and Rh, as defined above, at any available point of attachment. When an alkyl group is described as being substituted with an alkyl group, such a phrase is used interchangeably with "branched alkyl group."

The term "cycloalkyl" is a species of alkyl and is a group comprising about 3 to about 15 carbon atoms, without alternating or resonating double bonds between carbon atoms. It may also contain from 1 to 4 fused rings.

The term "aryl" refers to a group derived from a non-heterocyclic aromatic group having from six to about twenty carbon atoms and from one to four rings, which may be fused, connected by single bonds, or both. An aryl group may be substituted by one or more of alkyl, aralkyl, heterocyclic, heterocyclicalkyl, heterocycliccarbonyl, halo, hydroxyl, protected hydroxyl, amino, nitro, cyano, alkoxy, aryloxy, aralkyloxy, aroyloxy, alkylamino, dialkylamino, trialkylammonium, alkylthio, alkanoyl, alkanoyloxy, alkanoylamido, alkylsulfonyl, arylsulfonyl, aroyl, aralkanoyl, alkyloxycarbonyl, aralkyloxycarbonyl, aminocarbonyl, alkylaminocarbonyl, dialkylaminocarbonyl and the like.

The term "aralkyl" refers to an alkyl group bearing an aryl group substituent.

The term "heterocyclic", "heterocycle" or "heteroaryl" refers to a cyclic hydrocarbon group in which at least one of the ring positions is occupied by a heteroatom. A heterocyclic compound may have from one to about four rings, which may be fused, connected by single bonds, or both. A heterocyclic group may comprise from three to about twenty ring atoms, which atoms may be chosen from carbon, nitrogen, oxygen, or sulfur as long as at least one heteroatom is present. A heterocyclic group may have up to 1, 2, or 3 double bonds per ring, thus allowing for an aromatic system. A heterocyclic group may be substituted by one or more of alkyl, aryl, aralkyl, halo, hydroxyl, protected hydroxyl, amino, nitro, cyano, alkoxy, aryloxy, aralkyloxy, aroyloxy, alkylamino, dialkylamino, trialkylammonium, alkylthio, alkanoyl, alkanoyloxy, alkanoylamido, alkylsulfonyl, arylsulfonyl, aroyl, aralkanoyl, alkyloxycarbonyl, aralkyloxycarbonyl, aminocarbonyl, alkylaminocarbonyl, dialkylaminocarbonyl and the like.

The term "alkenyl" refers to a monovalent alkene group comprising up to about 20 carbon atoms which contains at least one double bond between carbon atoms. The alkene group may be straight chained or branch chained. Examples include vinyl, propenyl, butenyl and pentenyl groups.

The term "alkynyl" refers to a monovalent alkyne group comprising up to about 20 carbon atoms which contains at least one triple bond between carbon atoms. The alkyne group may be straight or branch chained. Examples are propynyl, butynyl and pentynyl.

The term "heteroatom" means an atom other than carbon or hydrogen, but is generally associated with the atoms N, O, or S, selected on an independent basis.

The term "halogen" or "halo" refer to fluorine, chlorine, bromine, or iodine.

The terms "alkoxy," "aryloxy" and "aralkyloxy" refer to a chemical group in which an oxygen atom is covalently bound to an alkyl, aryl, or aralkyl group, respectively.

The terms "alkanoyl," "aroyl" and "aralkanoyl" refer to chemical groups in which a carbonyl group is covalently bound to an alkyl, aryl, or aralkyl group, respectively.

The term "heterocyclicalkyl" or "heterocycliccarbonyl" refers to chemical groups in which a heterocyclic group is covalently bound to an alkyl or carbonyl group, respectively.

When a group is termed "substituted," unless otherwise indicated, this means that the group contains from 1 to 3 substituents thereon.

When a functional group is termed "protected," this means that the group is in a temporary, modified form to inhibit the participation of the protected site in a particular reaction sequence intended to effect some change elsewhere in the molecule. Suitable protecting groups for the compounds of the present invention will be recognized from the present application taking into account the level of skill in the art, and with reference to standard textbooks, such as Greene, T. W. et al. "Protective Groups in Organic Synthesis" Wiley, New York (1991). In addition, examples of suitable protecting groups are presented throughout the specification.

In some of the glycopeptide compounds of the present invention a hydroxyl-protect group might be required. Such conventional protecting groups consist of known groups, which are used to protectively block the hydroxyl group during the synthetic procedures described herein. These conventional blocking groups are readily removable; i.e., they can be removed, if desired, by procedures that will not cause cleavage or other disruption of the remaining portions of the molecule. Such procedures include chemical and enzymatic hydrolysis, treatment with chemical reducing or oxidizing agents under mild conditions, treatment with a transition metal catalyst, a nucleophile and catalytic hydrogenation.

Examples of suitable C-6 hydroxyl protecting groups include, but are not limited to, tyiethysilyl, t-butyldimethylsilyl, o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

The glycopeptide compounds of the present invention are useful per se and in their pharmaceutically acceptable salt and ester forms for the treatment of bacterial infections in animal and human subjects. The term "pharmaceutically acceptable ester, salt, or hydrate" refers to those esters, salts, or hydrated forms of the compounds of the present invention, which would be apparent to the medicinal chemist. Such forms include, but are not limited to, those that are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel glycopeptide compounds of the present invention, particularly the vancomycin-like glycopeptide compounds disclosed herein.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2—hydroxyelhanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, undecanoate and the like.

A strategy to introduce a suitable set of protecting groups and to differentiate the C-6 hydroxyl group from all other hydroxyl groups of a glycopeptide having a hexose residue at amino acid number four ($A_4$) is illustrated below in Scheme 1, showing functionalization of the glucose C-6 hydroxyl of vancomycin, wherein Alloc-Su is N-(allyloxycarbonyloxy) succinimide.

In general, introduction of the substituent containing the linker group on the vancosamine nitrogen is preferably by reductive amination, either direct or to a peptide-protective species. In general, introduction of the polar group at $C_6$ is preferably by azide displacement/reduction, amine nucleophilic displacement, and/or acylation.

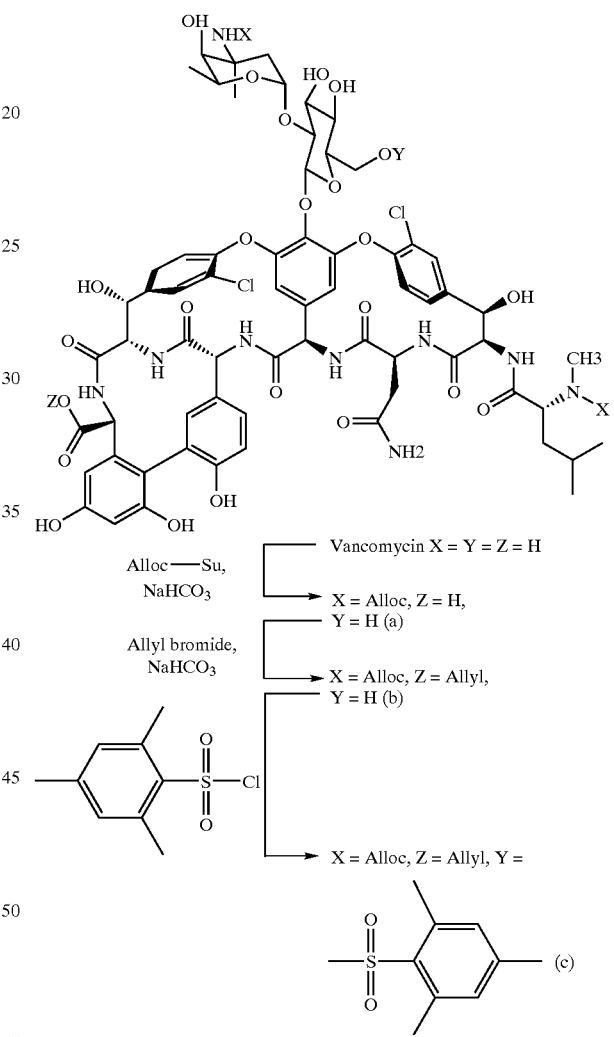

Scheme 1

Protection of both arnines by a similar group requires using excess acylation reagent while selective protection of the N-methyl leucine residue is known, allowing selective functionalization of the vancosamine amnine group. See, Pavlov et al., J. Antiobiotics, 1993, 46, 1731. Selectively, introducing the mesitylenesulfonyl group at the glucose-6-position differentiates this position from the other hydroxyl groups and allows further reaction to displace the mesitylenesulfonyl group, affording many derivatives. A variety of finctional groups are introduced at the glucose-6 position by using common methods for nucleophilic displacement of primary arylsulfonyl groups directly, or by further synthetic modification of initial displacement products, including azido and iodo groups. For example, the jodo group is displaced by a variety of nucleophiles to produce additional C-6 derivatives. A preferred nucleophile is a thiol compound, especially a heterocyclic thiol. Modification of an azido group at the 6-position is performed, e.g., by reducing the azido group to an amino group, which in turn is finctionalized by means of reductive alkylation, nucleophilic substitution, or other amino-group reactions well known to those skilled in the art. These approaches are illustrated in many examples. In a preferred embodiment of the invention, an azido group is partially reduced by reaction with a phosphine compound to produce an iminophosphorane.

More specifically, the amino substituents of vancomycin are protected as indicated while introducing a mesitylenesulfonyl functional group at the $C_6$ position. The allyloxycarbonyl groups are introduced by reaction of vancomycin hydrochloride in aqueous solution with N-(allyloxycarbonyloxy) succinimide contained in an organic solvent such as acetone. A preferred procedure is to treat the aqueous solution of vancomycin with the organic solvent solution of succirnide.

This resulting solid product is reacted with an allyl halide reactant such as allyl bromide in the presence of an alkali metal bicarbonate to form an allyl ester of the carboxyl and protect that position. The resulting allyl ester is then reacted with a compound which will introduce a functional group such as mesitylenesulfonyl chloride by reaction in a solvent such as pyridine so as to introduce the mesitylenesulfonyl moiety at the $C_6$ hydroxy. This compound is then reacted with an alkali metal halide such as KI to introduce I at the $C_6$ position. The protective allyl group is then removed conventionally such as with a palladium compound and a phosphinobutane.

In the next step, the intermediate is reacted with allyloxycarbonyl succinimide to protect the secondary nitrogen while leaving the primary nitrogen unprotected. At this stage the intermediate can be reacted with an aldehyde such as the benzyloxybenzaldehyde as in Example 5.4 to introduce a benzyloxybenzyl group at the vancosamine nitrogen. Similarly, other aldehydes can be reacted with the same or similar intermediate to form other derivatives, such as the use of the aldehyde phenylbenzaldehyde to introduce the K—$Ar_1$—Z—$Ar_2$ moieties of the compounds of the tables. Similarly, aldehydes or other reactive compounds can be used in a known manner to introduce the K—$Ar_1$—Z—$Ar_2$ derivatives of the compounds of the tables.

After the vancosamine is suitably substituted, the intermediate is reacted with an alkali azide to form an azide which is then reacted with a phosphine for conversion to the amine. Obviously substituted amines such as the substituents shown in this position in the compounds of the tables can be provided using these reations.

After the vancosamine amine polar group is introduced, the protected secondary amine is deprotected to produce the final product.

A similar procedure for preparation of the glycopeptides of the invention is shown in the following reaction scheme 2 where K—$Ar_1$—Z—$Ar_2$ is as described above, and Fmoc is Fluorenylmethoxycarbonyl, and $NR_2R_2^1$ is the reactant to introduce the amine substituent. In this reaction with XCHO, deblocking is carried out as described, and X is the K—$Ar_1$—Z—$Ar_2$ substituent on the vancosamine nitrogen.

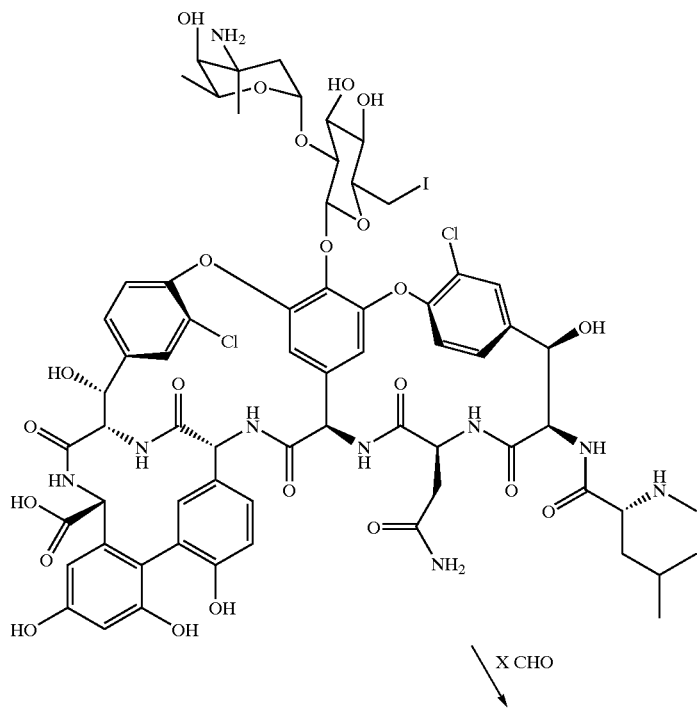

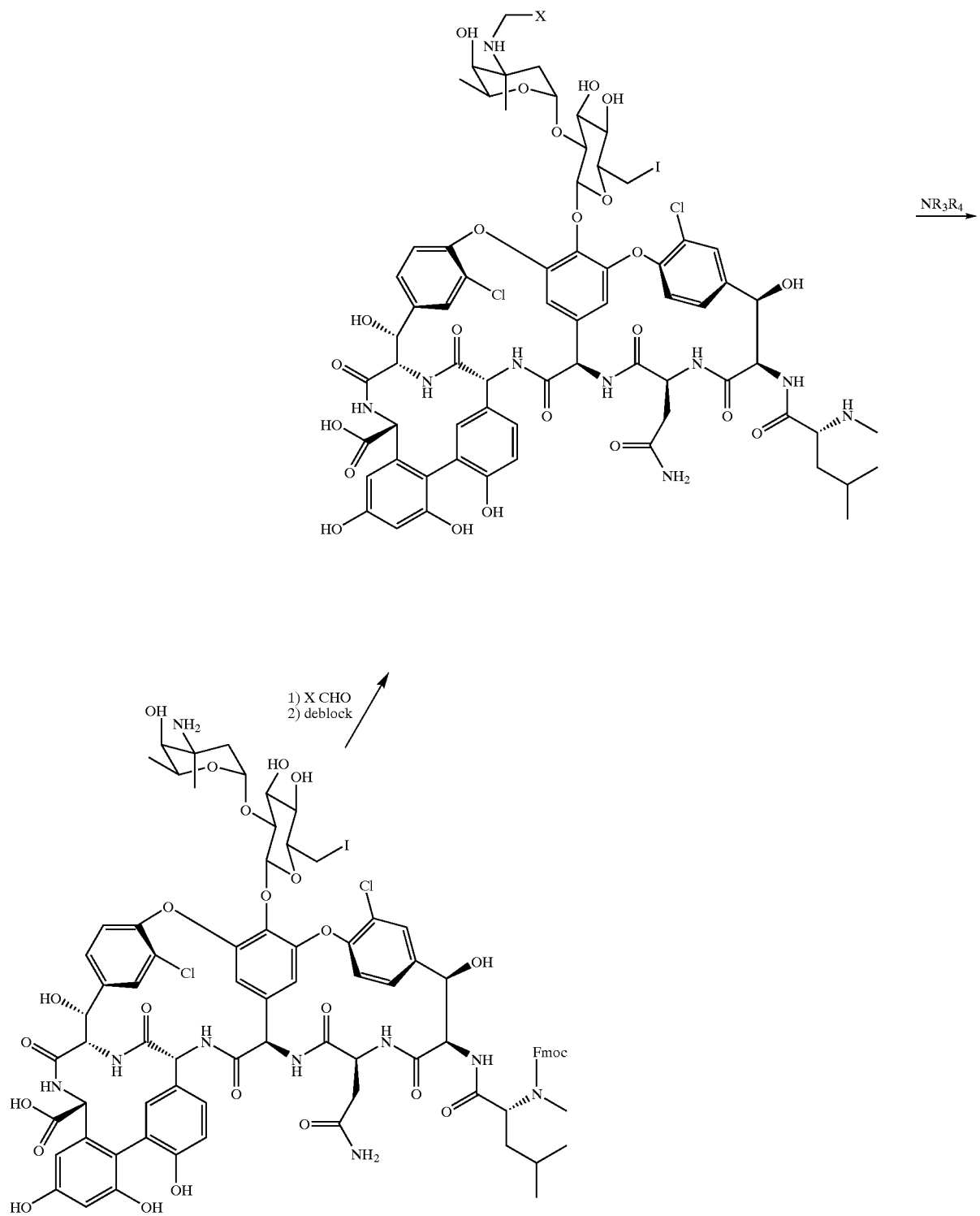

-continued

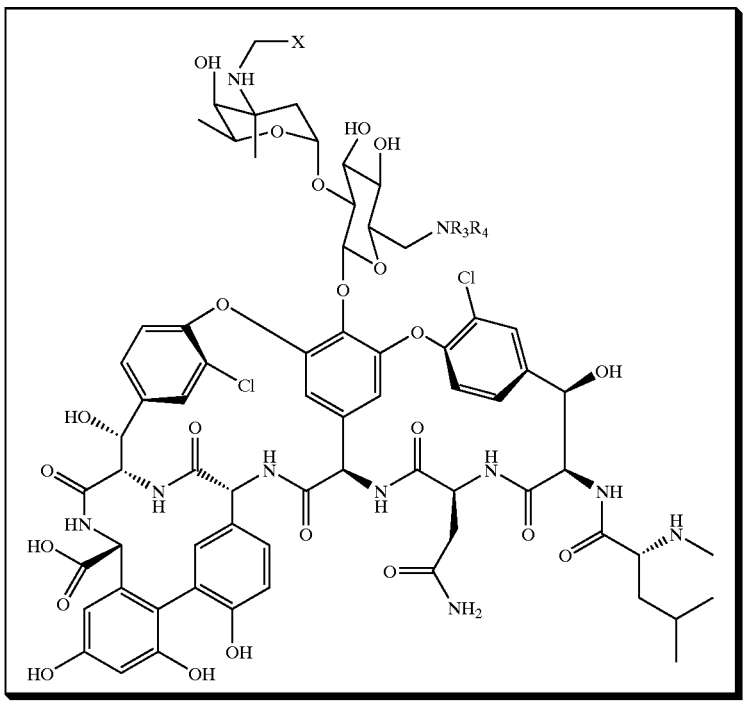

In a preferred embodiment of the invention, the vancomycin analog and its pharmaceutically acceptable salt is described by the Formula 1, depicted above, in which the group R represents a group

in which $R_3$ and $R_4$ may independently be H, $(C_{1-12})$alkyl, aryl$(C_{1-3})$alkyl, heterocyclic$(C_{1-3})$alkyl, $(C_{1-12})$alkylcarbonyl, arylcarbonyl, or heterocyclic-carbonyl, said alkyl, aryl, heterocyclicalkyl, being optionally substituted with 1–3 groups of $R_1$; or in which $R_3$ and $R_4$ may be linked by one or more covalent bonds to form one or more rings of 3–20 members each;

K is a carbonyl, sulfonyl, $(C_{1-3})$alkyl, Oxy$(C_{23})$alkyl, $(C_{1-3})$alkylcarbonyl, or $(C_{1-3})$-alkyloxycarbonyl;

Z is a carbonyl, sulfonyl, $(C_{1-3})$alkyl, $(C_{1-3})$alkyloxy, Oxy$(C_{1-3})$alky $(C_{1-3})$-alkyloxy$(C_{1-3})$alkyl, aminocarbonyl, carbonylamino, aminosulfonyl or, sulfonylamino;

$Ar_1$, is aromatic or heterocyclic, each optionally monosubstituted or disubstituted with $R_1$; and $Ar_2$ is aromatic or heterocyclic, each optionally monosubstituted, disubstituted, or trisubstituted with $R_1$;

$R_1$ is halo including chloro, bromo, iodo or fluoro, $R_2$, CN, $CF_3$, $OCH_xF_{(3-x)(x=0-3)}$, $NHSO_2R_2$, $OR_2$, $SR_2$, $N(R_2)_2$, $N(R_2)3$, $C(O)N(R_2)_2$, $SO_2N(R_2)_2$, $C(O)R_2$, $OC(O)R_2$, or $NHC(O)R_2$, and wherein $R_2$ independently represents H, aryl, straight- or branched-chain $(C_{1-3})$alkyl group, aryl$_{(C1-3)}$alkyl, heterocyclic, heterocyclic$(C_{1-3})$alkyl, alkylsulfonyl, arylsulfonyl and the like. When two $R_2$ groups are present, they may optionally be linked by covalent bonds to form one or more rings. Said rings may be aromatic, aliphatic, or heterocyclic.

In yet another preferred embodiment of the invention, the group K is a carbonyl, sulfonyl, or $CH_2$ group. The R group is more preferably $Nh_2$.

A representative exanple of a preferred embodiment of the vancomycin analog compounds of the present invention is depicted below:

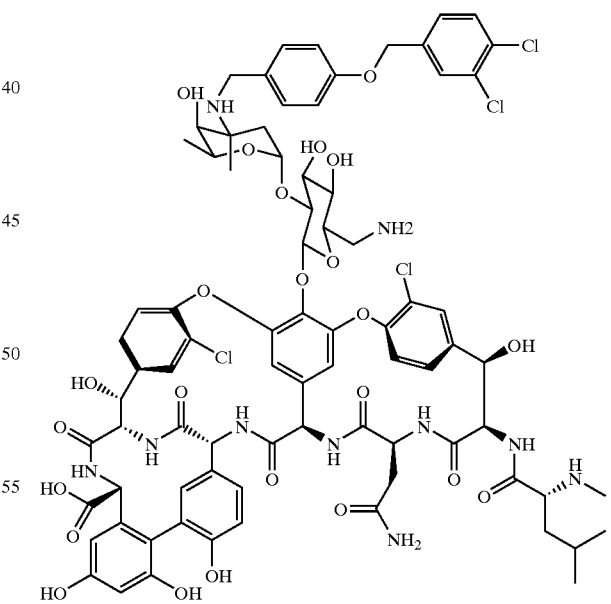

This compound is Entry Number 13 in Table 2.

The synthesis of the target compound is completed by removing any protecting groups that may be present in the penultimate intermediate using standard techniques that are well known to those skilled in the art. The deprotected final product is then purified, as necessary, using standard techniques such as ion exchange chromatography, reverse phase HPLC, MPLC on reverse phase polystyrene gel and the like, or by recrystallization.

The final product may be characterized structurally by standard techniques such as NMR, IR, MS and UV. For ease of handling, the final product, if not crystalline, may be lyophilized from water to afford an amorphous, easily handled solid.

The compounds of the present invention are valuable antibacterial agents active against various gram-positive and, to a lesser extent, gram-negative bacteria. Accordingly, these compounds find utility in human and veterinary medicine.

Many of compounds of the present invention are biologically active against VRE/MRSA/MRCNS. In vitro antibacterial activity is generally predictive of in vivo activity. It is contemplated that the compounds of the present invention will be administered to a mammal infected with a susceptible bacterial organism.

Using standard susceptibility tests, the compounds of the invention are determined to be active against VRE/MRSA.

The compounds of the invention can be formulated in pharmaceutical compositions by combining the compound with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampoules, or in multidose containers. The injectable compositions may take such forms as suspensions, solutions, or emulsions in oily or aqueous vehicles, and may contain various formulating agents. Alternatively, the active ingredient may be in powder (lyophilized or non-lyophilized) form for reconstitution at the time of delivery with a suitable vehicle, such as sterile water. In injectable compositions, the carrier is typically comprised of sterile water, saline, or another injectable liquid, e.g., peanut oil for intramuscular injections. Also, various buffering agents, preservatives and the like can be included.

Topical applications may be formulated in carriers such as hydrophobic or hydrophilic base formulations to provide ointments, creams, lotions, in aqueous, oleaginous, or alcoholic liquids to form paints or in dry diluents to form powders.

Oral compositions may take such forms as tablets, capsules, oral suspensions and oral solutions. The oral compositions may utilize carriers such as conventional formulating agents and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and be made isotonic.

The invention described herein also includes a method of treating a bacterial infection in a mammal in need of such treatment comprising administering to said mammal a compound of Formula I in an amount effective to treat said infection.

The preferred methods of administration of the Formula I antibacterial compounds include oral and parenteral, e.g., i.v. infusion, i.v. bolus and i.m. injection.

The invention is further described in connection with the following non-limiting examples.

EXAMPLES

5.1. Preparation of N,N'-Diallyloxylcarbonyl-glucose-C6-iodide vancomycin Allyl Ester A

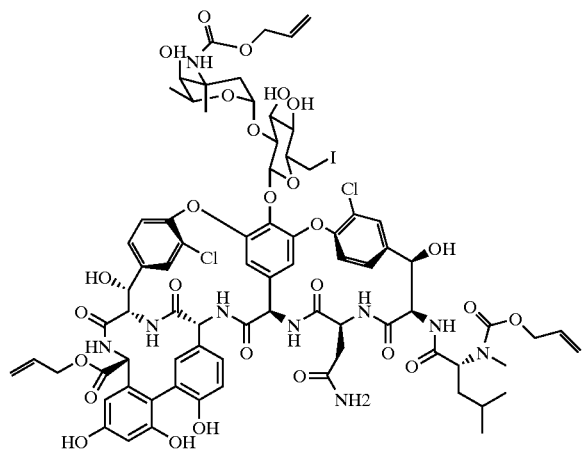

Step 1: N,N'-diallyloxycarbonyl Vancomycin (a)

To a solution of vancomycin-HCL (13 g, 8.7 mmol) in 105 mL water is slowly added 80 mL acetone. A 30 mL aqueous solution of NaHCO3 (1.54 g, 18.3 mmol) is then added over 5 minutes affording a thick white slurry. After stirring 10 minutes the suspension is treated with a solution of Nallyloxycarbonyloxy)succinimide (18 g, 90 mmol) in 70 mL acetone. Within a few hours the reaction became clear and stirred at room temperature for 36 hours. TLC (6:4:1, chloroform-methanol-water) shows no vancomycin (baseline) remaining and one predominant glycopeptide product (Rf=0.3). The crude reaction mixture is treated with 1-butanol (100 mL) and evaporated to dryness under reduced pressure. The solid is dissolved in 50 mL methanol and precipitated by addition to 300 mL diethyl ether. Any chunks are crushed and the white suspension allowed-to settled for 1 hour at 4° C. Approximately 200 mL, of the clear supematant is decanted and the remaining suspension centrifuged and the supernatant decanted. The white solid is mixed vigorously with 240 mL acetone, the suspension centrifuged and the supematant decanted. The solid is dissolved in methanol, diluted with 300 mL toluene and evaporated under reduced pressure affording (a) (15.5 g, containing a trace of the NHS impurity) which could be used without further purification. If it is desirable removal of the NHS; the solid is dissolved in a minimum of methanol/DMF (1:1) and precipitated by addition to water. The suspension is mixed well, the suspension centrifuged and the supernatant decanted. The white solid is dissolved in methanol to combine fractions, diluted with excess toluene, evaporated under reduced pressure, and dried in vacuo. Preparation of N-(allyloxycarbonyloxy)succinimide is reported in Int. J. Peptide Protein Res 1991, 37, 556–564.

Step 2: N,N'-diallyloxylearbonyl-vancomycin Allyl Ester (b)

Compound (a) (5 g, 3 mmol) is dissolved in 28 mL DMSO under an argon atmosphere (1 hour with stirring). Powdered $Na.HCO_3$ (2.5 g, 30 mnmol) is added and the suspension stirred 10 minutes followed by addition of allyl bromide (1.3 mL, 15 mmol). Stirring is continued for 7 hours, at which time TLC shows the disappearance of (II) and one predominate product. The reaction is slowly diluted with acetone (ca. 25 mL) until the precipitate, formed upon addition, is just redissolved. This solution is vacuum filtered (removing the insoluble $NaHCO_3$) into a flask containing 200 mL acetone and 450 mL diethyl ether. The flask is swirled occasionally during filtrate addition to disperse the mixture of white precipitate and oil that formed. The reaction flask and filter are rinsed with 10 mL acetone-methanol (1:1). The filtrate/suspension is stored at 4° C. for 16 hours with occasional swirling. The precipitate and oil coated the flask leaving a clear supernatant that is decanted. The solid mass is rinsed with acetone, dried under high vacuum, and dissolved in 10 mL DMF-methanol (1:1). This solution is precipitated by addition to 180 mL water (600 mL in 6 centrifuge tubes). The suspension is mixed, chunks crushed, centrifuged, and the supernatant decanted. The solids are combined in methanol-acetone, diluted with toluene, evaporated under reduced pressure, and dried in vacuo affording (b) (4.5 g). TLC: Rf=0.67; (chloroform-methanol-water, 6:4:1). An analytical sample is prepared by separation on HPLC; (Method A; 30 minutes linear gradient of 25% to 60% acetonitrile; flow rate=7.5 mL/min.) affording (b), Ret. time=24 minutes; LRESI-MS calc for 2:1655.5; [M+H]+=1657; [M-vancosamine+H]+=1431.

Step 3: N,N'-diallyloxycarbonyl-glucose-C6-mesitylenesulfonyl vancomycin allyl ester (c)

To a stirred solution of compound (b) (370 mg, 0.22 mmol) in 2.5 mL anhydrous pyridine under an argon atmosphere at 4° C. is added 0.5 mL of 1.4 M solution of mesitylenesulfonyl chloride in pyridine. The temperature is maintained at 4° C. for 24 hours at which time the reaction is precipitated by addition to 50 mL diethyl ether (2×25 mL in two 50 mL centrifuge tubes). The suspension is centrifuged and the supernatant decanted. The solids are combined by dissolving in methanol and evaporated under reduced pressure. Separation by HPLC (Method A; 40 minutes linear gradient of 30% to 75% acetonitrile; flow rate=7.5 mL/minutes) affords starting material (b) (64 mg) and (c) (202 mg, 50%, 60% based on recovered (b). Ret. time=28 minutes; TLC:Rf=0.7 (chloroform-methanol-water, 50:21:4). LRESI-MS calc for C86h97N9O3OSIC12:1837.5; [M+H]+=1839; [M-vancosarnine+H]+=1614; [M-disaccharide +H]+=1267.

Step 4; N,N'-diallyloxylcarbonyl-glucose-C6-iodide-vancomycine allyl ester (A)

N,N'-diallyloxycarbonyl-glucose-C6-mesitylenesulfonyl-vancomycin allyl ester (0.2 mmol, 367 mg) and KI (2 mmol, 332 mg) are heated in 4 mL of DMF at 80° C. for 16 h. The reaction is allowed to reach ambient temperature, and the product is precipitated by addition of 100 mL of $H_2O$. The product is filtered, washed with water and dried under high vacuum, affording 310 mg of a white solid, A.

5.2. Preparation of Glucose-C6-iodide-vancomycin B

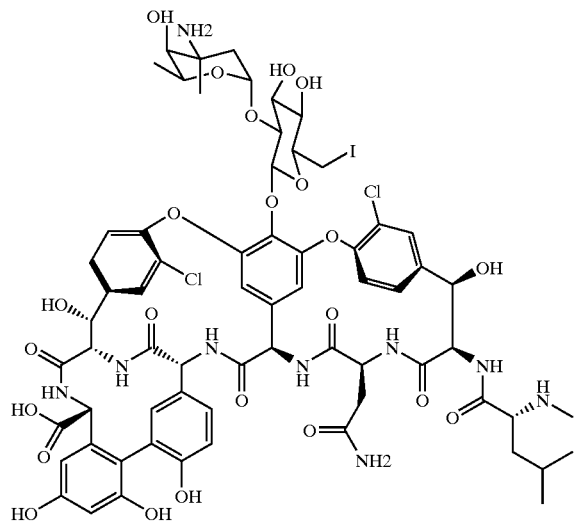

B

N,N'-diallyloxycarbonyl-glucose-$C_6$-iodide-vancomycin allyl ester A (1.7 mmol, 310 mg) is dissolved in 4 mL of DMF containing piperidine (2 mmol, 211 IEL). To the reaction mixture is added a 1 mL solution of tris (dibenzylideneacetonc)-dipalladium(0) (0.04 mmol, 17 mg) and 1,4-bis(diphenylphosphino)-butane (0.04 mmol, 17 mg) in THF, which solution is allowed to react for 5 min. prior to addition. After 1 h. the product is precipitated by addition of 100 mL of ether. The product is filtered and washed with additional ether to provide B. Retention time=0.73 min.

5.3. Preparation of N'-allyloxycarbonyl-glucose-C6-iodovancomycin C

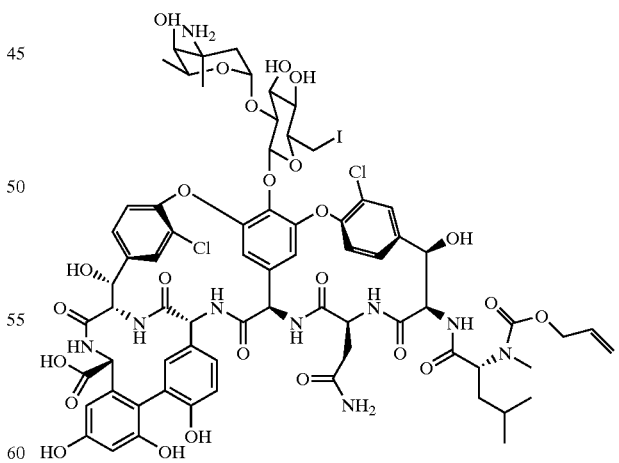

C

To a stirring solution of B (0.2 mmol, 3 10 mg) and $NaHCO_3$ (0.6 mmol, 50 mg) in 10 mL of 1:1 dioxane/$H_2O$ cooled in an ice bath is added dropwise a solution of N-(allyloxycaobonyloxy)succinimide (0.3 mmol, 60 mg) in 1 mL of dioxane. The reaction is allowed to stir overnight, during which time the solution reaches ambient temperature. The product is purified by reverse-phase HPLC, which after lyophilization affords 103 mg of monoalloc C as the TFA salt. Retention time=1.29 min.

5.4. Preparation of N-4-(3–4-dichlorobenzyloxy)benzyl-N'-alloc-glucose-C6-iodovancomycin D

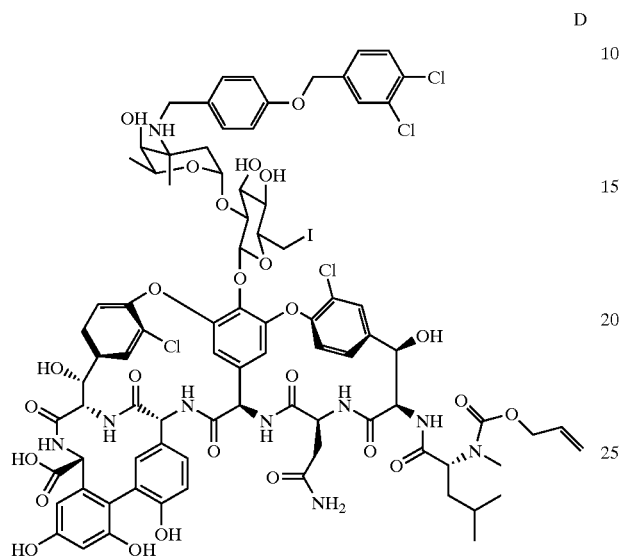

D

To a solution of C (0.035 mmol, 62 mg) and 4-(3-4-dichlorobenzyloxy)benzaldehyde (0.25 mmol, 70 mg) in 2 mL of DMF containing 1% (v/v) of HOAc is added NaBH(OAc)$_3$ (0.25 mmol, 53 mg). After 2 h, an additional 50 mg of NaBH(OAc)$_3$ is added, and the reaction is allowed to stand at ambient temperature for 15 h. The product is precipitated by addition of 60 mL of H$_2$O to the solution. The solid is filtered and dried in vacuo, affording 56 mg of D as a white solid. Retention time =1.98 min.

5.5. Preparation of N-4-(3-4-Dichlorobenzyloxy)benzyl-N'-allyloxycarbonyl-glucose-C6-amino-vancomycin E

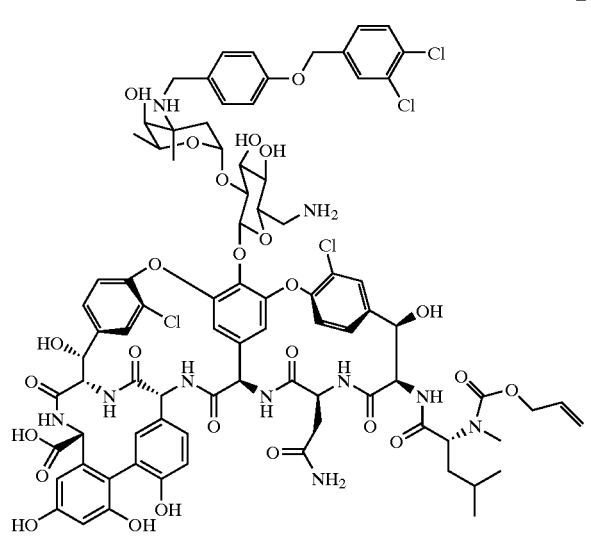

E

A solution of D (0.02 mmol, 37 mg) and NaN$_3$ (0.3 mmol, 20 mg) in 1 mL of DMF is stirred at 60° C. for 4 h. The reaction is then stirred at 40CC for an additional 15 h. The reaction mixture is allowed to reach ambient temperature and solid NaN$_3$ is removed by filtration. The product is precipitated by addition of 40 nL of ether, filtered and washed with methylene chloride. The resulting azidovancomycin is dissolved in 3 mL of 4:1 THF/H$_2$O, and Ph$_3$P(50 mg) is then added to the mixture. The reaction is stirred for 16 h. at 40° C. Solvent is removed by rotary evaporation. The residue is triturated in methylene chloride and filtered, affording 40 mg of E. Retention time=1.79 min.

5.6. Preparation of N-4-(3–4-Dichlorobenzyloxy)benzyl-N-glucose-C6-amino-vancomycin 13

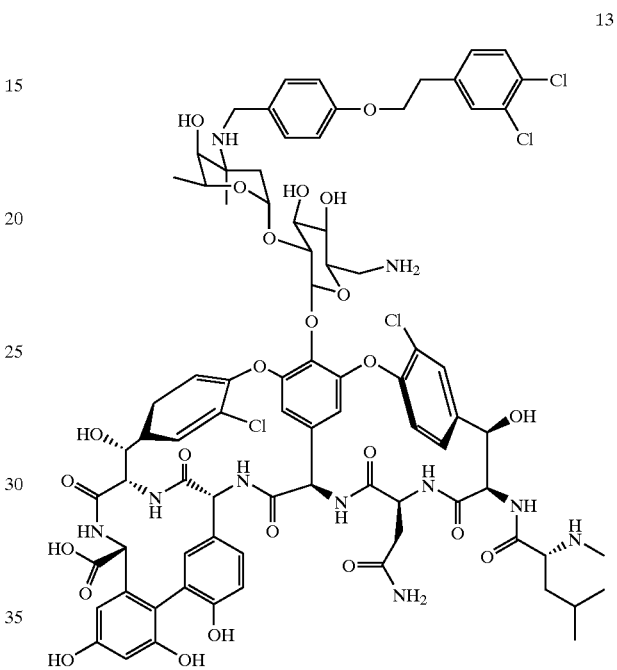

13

To compound E in 9:1 (v/v) DMF/piperidine is added a 1 mL solution in THF of tris(dibenzylideneacetone)-dipalladium(O) (0.01 mmol, 4 mg) and 1,4-bis(diphenylphosphino)-butane (0.01 mmol, 4 mg), which solution is allowed to react for min. prior to addition. After 1 h. the product is precipitated by addition of 10 mL of ether, filtered, and washed with additional ether. The solid is taken up in DMF and filtered to remove residual Pd. Removal of solvent in vacuo affords 17 mg of crude 13. A 4 mg portion of crude material is purified by reverse-phase HPLC to afford 1.4 mg of pure 13 as the TFA salt. Retention time= 1.39 min; Mass Spec. $[M+H]^{2+}$ 856

5.7. Preparation of Additional Compounds

Using methods similar to the method described above, compounds 1–12 and 14–24 are prepared and purified using reverse phase HPLC. The identities of the chemical groups comprising the lipid-like substituent, K—Ar$_1$—Z—Ar$_2$, and the polar substituent R, in particular where R=NR$_2$R$_3$, are illustrated in Table 2, appended to the specification. Vancomycin analogs comprising a more conventional substituent at the amine nitrogen of vancosamine are illustrated in Table 1. The retention times of each of the compounds, as well as their putative molecular weights, are also presented in Tables 1 and 2. Of interest is the greater retention time (on average about a 17% increase in retention time) observed for the compounds of Table 2 over the compounds of Table 1, regardless of the nature of the substituent on the glucose C-6 position. The retention times support the proposition that the compounds of Table 2 exhibit an increased lipophilicity over the compounds of Table 1.

The chemical names of the compounds listed in Table 2 are: Glucos-6-amino-N-4-(3,4-dichlorobenzyloxy)benzyl-vancosamino-vancomycin, 13; N-(3-Pyridyl)methyl-glucos-6-amino-N4-(3,4-dichlorobenzyloxy)benzyl-vancosamino-vancomycin, 17; N-Glycyl-glucos-6-amino-N-4-3,4-dichlorobenzyloxy)benzyl-vancosamino-vancomycin 18; N-0-Alanyl-glucos-6-amino-N4-(3,4-dichlorobenzyloxy) benzyl-vancosamino-vancomycin 18; N-D-Alanyl-glucos-6-amino-N4-(3,4-dichlorobenzyloxy)benzyl-vancosamino-vancomycin, 19; N-L-Prolyl-glucos-6-amino-N-4-(3,4-dichlorobenzyloxy) benzyl-vancosamino-vancomycin, 18; N-P-Alanyl-glucos-6-amino-N-4-(3,4-dichloro benzyloxy) benzyl-vancosamino-vancomycin, 19; N-L-Lysyl-glucos-6-amino-N4-(3,4-dichlorobenzyloxy)benzyl-vancosamino-vancomycin, 20; N-L-(3-thiazolyl)alanyl-glucos-6-amino-N-4-(3,4-dichlorobenzyloxy)benzyl-vancosamino vancomycin, 21; N-L-(2-thienyl)alanyl-glucos-6-amino-N4-(3,4-dichlorobenzyloxy)benzyl-vancosamino-vancomycin, 22; N-L-Asparagyl-glucos-6-amino-N-4- (3,4-dichlorobenzyloxy)benzyl-vancosamino-vancomycin, 23; N-D3-pyridyl)alanyl-glucos-6-amino-N4(3,4-dichlorobenzyloxy)benzyl-vancosamino-vancomycin, 24.

These compounds exhibit desirable levels of antibiotic activity when tested against a panel of bacterial strains, including certain vancomycin-resistant strains, as described in greater detail, below. The compounds listed in Table 2 consistently provide for at least a two- to four-fold increase in activity, however, compared to the compounds listed in Table 1, at least for those strains of bacteria which exhibit the greatest resistance to vancomycin and teicoplanin.

5.8. In Vitro Assay Utilizing a Panel of Bacterial Strains 5.8.1. Assay Protocol National Committee for Clinical Laboratory Standards (NCCLS) guidelines [Methods for Dilution Antimicrobial Susceptibility Tests for Bacteria that Grow Aerobically-Fourth Edition; Approved Standard (NCCLS Document M7-A$_4$, January 1997)] are used to establish the assay, although variations are made to optimize the published method according to the specific needs of the present investigation.

The test panel currently includes eight enterococci and 13 staphylococci, which are selected based upon their antibiotic susceptibility profiles. The methicillin-sensitive Staphylococcus aureus (MSSA) strain MB2985 (Smith isolate) is used to assesses the potential for serum protein binding of the compounds. The paired Gram-negative strains ASP #49 (envA-) and ASP #50 (envA+) (M. Salvatore/N. Lee) are included to judge membrane effects. Table 3 presents a detailed description of the strains included in the panel, including some of the sources of the strains of bacteria.

Relevant antibiotic controls include the glycopeptide antibiotic vancomycin and the penem antibiotic Schering 29482, which exhibits reduced activity in the presence of Human Serum Albumin or Fraction V, due to binding of the antibiotic. The glycopeptide antibiotic teicoplanin is included whenever possible.

5.8.2. Recommended Sources of Supplies

Trypticase Soy Broth (TSB) (Source: BBL, Becton Dickinson Microbiolgy Systems, Cockeysville, Md. 21030, U. S. A.)

Horse Serum (HS) (Source: GIBCO BRL Laboratories, Grand Island, N.Y. 14072, U. S. A.)

Mueller Hinton II Broth (MH II) (Source: BBL, Becton Dickinson Microbiology Systems, Cockeysville, Md. 21030, U. S. A.)

Brain Heart Infusion Broth (BHI) and Brain Heart Infusion Agar (BHI Agar) (Source: Difco Laboratories, Detroit, Mich. 48232, U. S. A.)

Human Serum Albumin, Fraction V (HSA) (Source: Calbiochem Corporation, La Jolla, Calif. 92037, U. S. A.)

5.8.3. Overnight Growth Medium

TSB, containing 10% HS* for vancomycin intermediate S. aurcus/methicillin-resistant S. aureus (VISA/MRSA) strains, is inoculated from an appropriate source (frozen broth or agar slant) and grown approximately 17 hr at 35° C. with shaking at 220 rpm. Cultures are grown in tubes with a volume of 5 ml for enterococci and 2 ml for all other strains.

* HS is aseptically added to TSB on top of normal volume of medium at time of use: 0.5 mL HS+5 mL TSB fi TSB+10% HS 5.8.4. Culture Dilution Four milliliter (4 ml) overnight culture is added to 36 ml physiological saline to obtain tenfold dilutions (enterococci). Overnight culture (0.4 ml) is added to 39.6 ml saline to obtain 100-fold dilutions (all strains except enterococci). Diluted cultures are maintained on ice until time of inoculation of test plates.

5.8.5. Plate Medium for Obtaining Titers of Overnight Cultures

The number of CFU/mL is determined on BHI agar plates, although this is not done routinely because titers of overnight cultures are relatively constant. The test media include:

BHI for enterococci and VISA/MRSA;

MH II (i.e., cation-adjusted Mueller-Hinton broth) for MRS, MSS and *E. coli.*;

MH II+HSA for MSSA is prepared as follows:

a. 2×MHII+86mg/ml HSA b. Dissolve 4.3 g HSA in 50 ml autoclaved 2x MH II.

c. pH to 7.0 by adding 2M MOPS, sodium.

d. Filter sterilize using 0.22 $\mu$m Corning cellulose acetate filter, used because of reported low protein binding.

e. 1×MH II+43 mg/ml HSA f. Dilute the 2×medium twofold and filter as above.

5.8.6. Preparation of Test Plates

Using a Denley liquid handling system (or similar automatic device), 100 $\mu$l×medium is added to each well in columns 2–12 of a 96-well microtiter dish. Using a multichannel pipettor, 100 $\mu$l 2×medium is added to each well in column 1. Plates may be filled on the day prior to assay, wrapped in plastic bags and refrigerated.

5.8.7 Preparation of Antibiotics

Vancomycin, Schering 29482, and teicoplanin are prepared on a weight per volume basis using 10 mM 3-(N-morpholino)propane-sulfonic acid (MOPS) buffer pH 7. Test compounds are received in solution in appropriate solvent (typically as 1 mg/ml in DMSO) or are dissolved in appropriate solvent prior to further dilution in 10 mM MOPS buffer, ph$_7$. Consistent with NCCLS guidelines, antibiotics are handled aseptically but are not otherwise sterilized.

5.8.8. Assay

100 $\mu$l appropriately diluted antibiotic solution is added to the first well of the designated row of the 96-well microtiter dish and serially diluted by twofold across the row using the Denley liquid handling system. With the aid of a Dynatech NEC 2000 inoculator, each well of the microtiter dish is inoculated with 1.5 $\mu$l diluted overnight culture, yielding approximately 1–5×106 CFU/ml for enterococci and approximately 3–7×105 CFU/ml for all other strains. Dishes are placed in stacks of no more than five, wrapped in plastic bags and incubated at 35° C.

Indication of result(s) type (% INH, IC$_{50}$, Zone size, etc.)

MIC=minimum inhibitory concentration ps 5.8.9. Interpretation of the Results on the Basis of Activity Presence or absence of growth is scored at 18–20 hr for strain MB2985 and for *E. coli.*, at 22–24 hr for all other strains. MIC is defined as the lowest concentration of antibiotic that allows no visible growth following incubation. The compounds of the present invention display adequate improvement over the activity exhibited by the control compounds. In particular, the results of panel testing of compound 13 are presented in Table 4.

5.8.10. In Vivo Mice Studies Protocol for the Methicillin-sensitive *Staphylococcus aureus* Septicemia Selected compounds of the invention are tested in an in vivo mouse model. Single dose subcutaneous antibiotic protection from septicemic infections is measured as described by Gill, C. J., J. J. Jackson, L. Gerckens, B. Pelak, R. Thompson, J. Sundelof, H. Kropp and H. Rosen. Antimicrob. Agents Chemother. 42:1996–2001 (1998). Survival is monitored for seven days. $ED_{50}$'s and $LD_{50}$'s are determined by the method of Knudsen and Curtis. J. Am. Stat. Assoc. 42:282–296 (1947). Septicemia is induced in 20 gram ICR (derived from CD-I) female mice by intraperitoneal infection with Staphylococcus aureus strain MB2985. Infection is given i.p. in Brain Heart Broth (BHB) at an infectious inoculum of $1.8 \times 10^7$ cfu/mouse. Drug is administered subcutaneously immediately after the infection is initiated.

The MIC is determined by microdilution in Mueller-Hinton broth (MHB) according to the National Committee for Clinical Laboratory Standards guidelines after incubation for 24 hours. Enterococci are tested in cation-supplemented Mueller-Hinton broth at $1.4 \times 105$ cfu/ml. MIC is defined as the lowest concentration of antibiotic, which inhibits visible growth.

Results for vancomycin and compound 13 are presented in Table 5.

What is more, pharmacokinetic studies show that compound 13 exhibits an unexpectedly greater bioavailability, faster clearance rate and/or more favorable tissue distribution than the bioavailability, clearance rate and/or tissue distribution observed for compound 2, which bears a chlorobiphenyl substituent on the amine nitrogen of vancosamine. These results indicate an improved likelihood that compound 13 and the other compounds listed in Table 2 might succeed in the clinic.

5.9. Additional Examples of Compounds of the Invention

As a further illustration of the types of compounds contemplated by the present invention, a Chart (Table 6) is provided listing over one hundred compounds.

The following definitions are set forth for clarification of the invention.

| | |
|---|---|
| DMF | N,N-dimethylformamide |
| THY | tetrahydrofuran |
| TFA | trifluoroacetic acid |
| EtOAc | ethyl acetate |
| MeOH | methanol |
| MeCN | acetonitrile |
| Tf | trifluoroacetyl group |
| DMSO | dimethyl sulfoxide |
| DIEA | diisopropylethylamine |
| All | in structural formulas refers to allyl group |
| HOBt | 1-hydroxybenzotriazole |
| CBz | benzyloxycarbonyloxy |
| Su | succinimidyl group |
| Alloc | allyloxycarbony |

TABLE 1

Compounds 1–12

| Entry K | Ar1 | Z | Ar2 | NR₂R₃ | Ret. Time (M + H)²⁺ |
|---|---|---|---|---|---|
| 1 | [structure] | | [biphenyl structure] | —NH₂ | 1.31 min. (835) |
| 2 —CH₂— | [phenyl] | bond | [chlorophenyl] | —NH₂ | 1.21 min. (824) |
| 3 —CH₂— | [phenyl] | bond | [chlorophenyl] | —NH–C(O)–CH₂–NH₂ | 1.21 min. (853) |
| 4 —CH₂— | [phenyl] | bond | [chlorophenyl] | —NH–C(O)–CH(CH₃)–NH₂ | 1.22 min. (860) |

TABLE 1-continued

Compounds 1–12

| Entry | K | Ar1 | Z | Ar2 | NR₂R₃ | Ret. Time (M + H)²⁺ |
|---|---|---|---|---|---|---|
| 5 | —CH₂— | *p-phenylene* | bond | *4-Cl-phenyl* | —NH—C(O)—CH(NH₂)—CH₃ (L-Ala) | 1.21 min. (860) |
| 6 | —CH₂— | *p-phenylene* | bond | *4-Cl-phenyl* | —NH—C(O)—(pyrrolidin-2-yl) (L-Pro) | 1.22 min. (873) |
| 7 | —CH₂— | *p-phenylene* | bond | *4-Cl-phenyl* | —NH—C(O)—CH₂—CH₂—NH₂ (β-Ala) | 1.21 min. (860) |
| 8 | —CH₂— | *p-phenylene* | bond | *4-Cl-phenyl* | —NH—C(O)—CH(NH₂)—(CH₂)₄—NH₂ (L-Lys) | 1.16 min. (888) |
| 9 | —CH₂— | *p-phenylene* | bond | *4-Cl-phenyl* | —NH—C(O)—CH(NH₂)—CH₂—(thiazol-4-yl) | 1.22 min. |
| 10 | —CH₂— | *p-phenylene* | bond | *4-Cl-phenyl* | —NH—C(O)—CH(NH₂)—CH₂—(thien-2-yl) | 1.24 min. (901) |
| 11 | —CH₂— | *p-phenylene* | bond | *4-Cl-phenyl* | —NH—C(O)—CH(NH₂)—CH₂—C(O)NH₂ (L-Asn) | 1.20 (882) |
| 12 | —CH₂— | *p-phenylene* | bond | *4-Cl-phenyl* | —NH—C(O)—CH(NH₂)—CH₂—(pyridin-3-yl) | 1.17 min. (898) |

TABLE 2

Compounds 13–24

| Entry | K | Ar1 | Z | Ar2 | NR₂R₃ | Ret. Time (M + H)²⁺ |
|---|---|---|---|---|---|---|
| 13 | —CH₂— | *p-phenylene* | —OCH₂— | *3,4-diCl-phenyl* | —NH₂ | 1.39 min. (857) |

TABLE 2-continued
Compounds 13–24
| Entry | K | Ar1 | Z | Ar2 | NR₂R₃ | Ret. Time (M + H)²⁺ |
|---|---|---|---|---|---|---|
| 14 | —CH₂— |  | —OCH₂— | 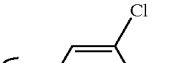 | 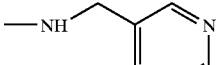 | 1.38 min. (902) |
| 15 | —CH₂— |  | —OCH₂— | 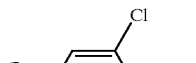 | 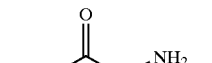 | 1.39 min. (886) |
| 16 | —CH₂— |  | —OCH₂— | 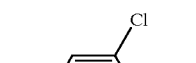 | 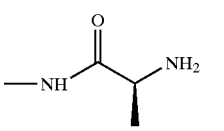 | 1.40 min. (892) |
| 17 | —CH₂— | 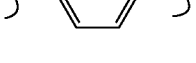 | —OCH₂— |  | 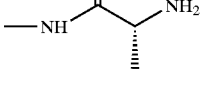 | 1.40 min. (892) |
| 18 | —CH₂— | 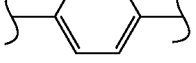 | —OCH₂— | 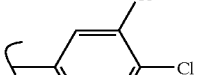 | 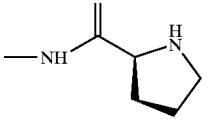 | 1.41 min. (905) |
| 19 | —CH₂— |  | —OCH₂— | 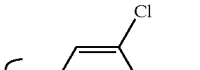 | 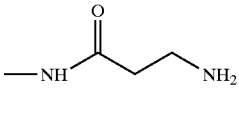 | 1.40 min. (892) |
| 20 | —CH₂— |  | —OCH₂— | 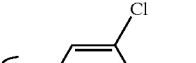 | 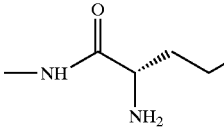 | 1.34 min. (921) |

TABLE 2-continued

Compounds 13–24

| Entry | K | Ar1 | Z | Ar2 | NR₂R₃ | Ret. Time (M + H)²⁺ |
|---|---|---|---|---|---|---|
| 21 | —CH₂— |  | —OCH₂— | 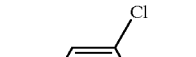 | | 1.42 min. (933) |
| 22 | —CH₂— | 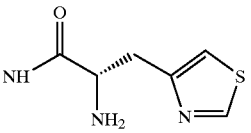 | —OCH₂— | 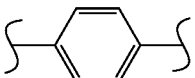 | | 1.43 min. (933) |
| 23 | —CH₂— | 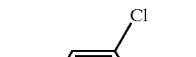 | —OCH₂— | 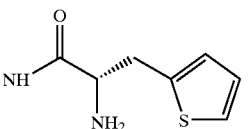 | | 1.39 (914) |
| 24 | —CH₂— | 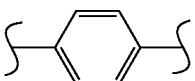 | —OCH₂— | 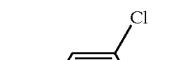 | | 1.35 min. (931) |

TABLE 3

Bacterial Strains for Assays

| | Strain | Phenotype[b] | | | | Source |
|---|---|---|---|---|---|---|
| | | Van[c] | Gent | Amp | 1pm | |
| Enterococci | | | | | | |
| E. faecium | RLA1 | S | S | R | R | Dr. B. Murray, Houston, TX |
| E. faecium | CL 4931 (VanA) | R | R | R | R | NY Hospital, NYC |
| E. faecium | CL 5053 (VanA) | R | R | R | R | Bellevue Hospital, NYC |
| E. faecium | CL 5242 (VanA) | R | R | R | R | Dr. Sahm, Wash. Univ. School of Med |
| E. faecalis | MB2864 | S | S | S | S | Merck Clinical Culture Collection |
| E. faecalis | CL 4877 (VanB) | R | R | S | S/I | Univ. of Maryland Hospital, Baltimore, MD |
| E. faecalis | CL 5244 (VanB) | R | S | S | S | Merck Clinical Culture Collection |
| E. gallinarum | CL 4886 (VanC) | I | R | S | S | Dr. Shlaes, Cleveland VA Hospital |
| Staphylococci | | | | | | |
| MSSA | MB2985[a] | S | S | S | S | Mouse pathogen (Smith strain) |
| MRSA | CL 3033 | S | | R | R | VA Hospital, East Orange, NJ |
| MRSA | COL | S | S | R | R | Dr. A. Tomasz, Rockefeller Univ., NYC |
| MRSA | MH 76 | | | | | |
| VISA/MRSA | CL 5705 | S | R | R | R | Mu 3; Dr. K. Hiramatsu, Juntendo Univ., Japan |
| VISA/MRSA | CL 5706 | I | R | R | R | Mu 50; Dr. K. Hiramatsu, Juntendo Univ., Japan |
| MRCNS (S. epi.) | CL 3069 | S | | | R | Univ. of Texas |
| MRCNS (S. hom.) | CL 227 | S | | | R | Temple Univ. Hosp., Philadelphia, PA |
| MRCNS (S. haem.) | CL 171 | S | | | R | Temple Univ. Hosp., Philadelphia, PA |
| MRCNS (S. haem.) | CL 202 | S | | | R | Temple Univ. Hosp., Philadelphia, PA |
| MRCNS (S. hom.) | CL 546 | S | | | R | Wilmington Med. Center, Delaware |

TABLE 3-continued

Bacterial Strains for Assays

| Strain | Van[c] | Phenotype[b] Gent | Amp | 1pm | Source |
|---|---|---|---|---|---|
| Gram-negative strains | | | | | |
| E. coli (envA*) ASP #49 | R | | | | Tet[R] envA* MB2884 (M. Salvatore/N. Lee) |
| E. coli (envA*) ASP #50 | R | | | | Tet[R] envA* MB2884 (M. Salvatore/N. Lee) |

[a]Selected for testing in presence of Human Serum Albumin, Frac. V.
[b]Minimum Inhibitory Concentration (MIC) Interpretive Standards ($\mu$g/ml)
(Excerpted from NCCLS. Jan. 1998. Vol. 18 No. 1. Document M7-MIC, Tables 2A, 2C and 2D.)

| Antibiotic | Susceptible | Intermediate | Resistant |
|---|---|---|---|
| Vancomycin (all but Enterobacteriaceae) | ≤4 | 8–16 | ≥32 |
| Gentamicin (enterococci) | ≤500 | — | >500 |
| Gentamicin (all but enterococci) | ≤4 | 8 | ≥16 |
| Ampicillin (enterococci) | ≤8 | — | ≥16 |
| Ampicillin (staphylococci) | ≤0.25 | — | ≥0.5 |
| Ampicillin (Enterobacteriaceae) | ≤8 | 16 | ≥32 |
| Imipenem (all but enterococci) | ≤4 | 8 | ≥16 |

[1]Abbreviations: Van, vancomycin; Gent, gentamicin; Amp, ampicillin; Ipm, imipenem

TABLE 4

Summary of MICs of Compound 13

| Strain | Vancomycin[b] | MIC ($\mu$g/ml) 13 #1 | 13 #2 | 13 #3 |
|---|---|---|---|---|
| E. faecium | | | | |
| RLA1 | 2 | ≤0.03 | 0.008 | 0.016 |
| CL 4931 (VanA) | 2048 | 2 | 0.5 | 1 |
| CL 5053 (VanA) | 2048 | 1 | 1 | 2 |
| CL 5242 (VanA) | 128 | 0.06 | 0.25 | 0.5 |
| E. faecalis | | | | |
| MB2864 | 2 | ≤0.03 | 0.12 | 0.25 |
| CL 4877 (VanB) | 2048 | 0.25 | 2 | 2 |
| CL 5244 (VanB) | 32 | 0.12 | 0.25 | 0.25 |
| E. gallinarum | | | | |
| CL 4886 | 16 | 1 | 0.25 | 1 |
| MSSA[a] | | | | |
| MB2985 | 1 | ≤0.03 | 0.008 | 0.016 |
| MB2985 + HAS | 1 | ≤0.03 | 0.008 | 0.008 |
| (N-fold MIC inc. + HSA) | (1) | | (1) | (0.5) |
| MRSA | | | | |
| CL 3033 | 0.5–1 | 0.25 | 0.12 | 0.12 |
| COL | 1 | 0.25 | 0.12 | 0.25 |
| MH 76 | 1 | 0.25 | 0.25 | 0.25 |
| VISA/MRSA | | | | |
| CL 5705 | 2–4 | 0.5 | 0.12 | 0.25 |
| CL 5706 | 4–8 | 0.5 | 0.12 | 0.5 |
| MRCNS | | | | |
| CL 3069 (S. epi.) | 2 | 0.06 | 0.03 | 0.06 |
| CL 227 (S. hom.) | 1 | 0.06 | 0.016 | 0.016 |
| CL 171 (S. haem.) | 2 | ≤0.03 | 0.03 | 0.06 |
| CL 202 (S. haem.) | 2 | 0.12 | 0.06 | 0.06 |
| CL 546 (S. hom.) | 1 | ≤0.03 | 0.016 | 0.016 |
| E. coli | | | | |
| ASP #49 (envA−) | 32 | 16 | 16 | 8 |
| ASP #50 (envA+) | 256 | >64 | 64 | 64 |

[a] The MIC for the control penem increases 32-fold, from 0.06 $\mu$g/mL in the absence of HSA to 2 $\mu$g/mL in the presence of HSA in the assays.
[b] Vancomycin is tested in duplicate for all strains except CL 5244, ASP #49 and ASP #50.
Overnight growth medium is TSB (+10% horse serum for VISA/MRSA). Test medium for enterococci and for VISA/MRSA is BHI broth; for MSSA, MRSA, MRCNS and E. coli, MH II broth ctg. 43 mg/ml Human Serum Albumin. Frac. V (HSA) as indicated for MB2985.

TABLE 5

Results of In Vivo Studies

| Compound | VAN | 13 |
|---|---|---|
| % Plasma Bound | 55 | nt |
| Test Organism | S. aureus | S. aureus |
| MB# | 2985 | 2985 |
| MIC ($\mu$g/ml) | 0.5 | 0.125 |
| # of Doses | 1 (0 hr) | 1 (0 hr) |
| # of LD$_{50}$'s | 69 | 69 |
| ED$_0$ (s.c., mg/kg) | ≤0.195 | 0.195 |
| ED$_{50}$ (s.c., mg/kg) | 1.167 | 0.390 |
| ED$_{100}$ (s.c., mg/kg) | 3.125 | 0.780 |
| ED$_{50}$/MIC | 2.33 | 3.12 |
| 95% C.L. | 0.67–2.03 | Nd |

Septicemia study is run in 20G ICR (derived from CD-1) female mice. Infection is given i.p. in BHB as $1.8 \times 10^7$ cfu/mouse, immediately followed by s.c. treatment.
The MIC inoculum is $1.4 \times 10^5$ cfu/mL in cation adjusted MHB.
Key: nd = not determined; nt = not tested; C.L. = confidence limit; BHB = Brain Heart Broth; MHB = Mueller-Hinton Broth

TABLE 6

Chart of Additional Compounds 1-132

| Example | K | Ar$_1$ | Z | Ar$_2$ | R |
|---|---|---|---|---|---|
| 1 | CH$_2$ | phenyl | CH$_2$-O- | 3,4-dichlorophenyl | NH$_2$ |
| 2 | C=O | phenyl | CH$_2$-O- | 3,4-dichlorophenyl | NH$_2$ |
| 3 | SO$_2$ | phenyl | CH$_2$-O- | 3,4-dichlorophenyl | NH$_2$ |
| 4 | CH$_2$CH$_2$ | phenyl | CH$_2$-O- | 3,4-dichlorophenyl | NH$_2$ |
| 5 | CH$_2$C(=O) | phenyl | CH$_2$-O- | 3,4-dichlorophenyl | NH$_2$ |

TABLE 6-continued

Chart of Additional Compounds 1–132

| Example | K | Ar₁ | Z | Ar₂ | R |
|---|---|---|---|---|---|
| 6 | C(=O) | 1,4-phenylene | CH₂-O | 3,4-dichlorophenyl | NH₂ |
| 7 | (CH₂)₂ | 1,4-phenylene | CH₂-O | 3,4-dichlorophenyl | NH₂ |
| 8 | O | 1,4-phenylene | CH₂-O | 3,4-dichlorophenyl | NH₂ |
| 9 | S | 1,4-phenylene | CH₂-O | 3,4-dichlorophenyl | NH₂ |
| 10 | CH₂ | 1,3-phenylene | CH₂-O | 3,4-dichlorophenyl | NH₂ |

TABLE 6-continued

Chart of Additional Compounds 1-132

| Example | K | Ar₁ | Z | Ar₂ | R |
|---|---|---|---|---|---|
| 11 | CH₂ | 2,5-thienyl | -CH₂-O- | 3,4-dichlorophenyl | NH₂ |
| 12 | CH₂ | 2,4-thienyl | -CH₂-O- | 3,4-dichlorophenyl | NH₂ |
| 13 | CH₂ | 2,4-dichlorophenyl | -CH₂-O- | 3,4-dichlorophenyl | NH₂ |
| 14 | CH₂ | 2,3,5-trichlorophenyl | -CH₂-O- | 3,4-dichlorophenyl | NH₂ |
| 15 | CH₂ | 3,4-dichlorophenyl | -CH₂-O- | 3,4-dichlorophenyl | NH₂ |

TABLE 6-continued
Chart of Additional Compounds 1–132
| Example | K | Ar₁ | Z | Ar₂ | R |
|---|---|---|---|---|---|
| 16 | 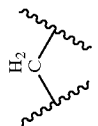 | 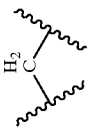 | 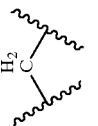 | 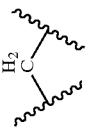 | 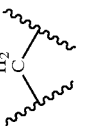 |
| 17 | 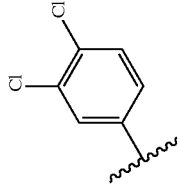 | 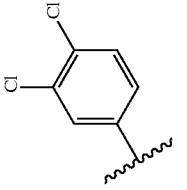 | 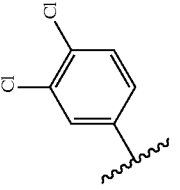 | 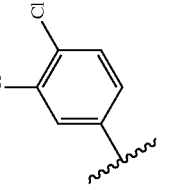 | 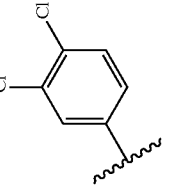 |
| 18 | 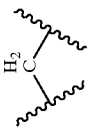 | 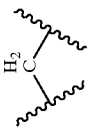 | 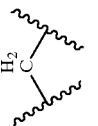 | 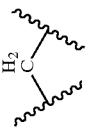 | 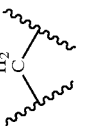 |
| 19 | 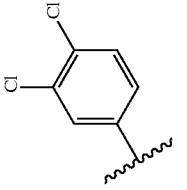 | 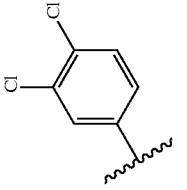 | 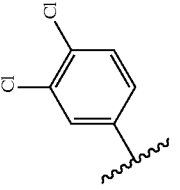 | 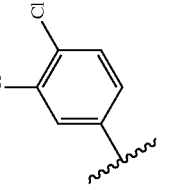 | 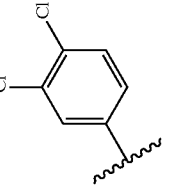 |
| 20 |  |  |  |  |  |

TABLE 6-continued

Chart of Additional Compounds 1–132

| Example | K | Ar₁ | Z | Ar₂ | R |
|---|---|---|---|---|---|
| 21 | CH₂ | 2,6-naphthyl | -CH₂-O-CH₂- | 3,4-dichlorophenyl | NH₂ |
| 22 | CH₂ | 2,7-naphthyl | -CH₂-O-CH₂- | 3,4-dichlorophenyl | NH₂ |
| 23 | CH₂ | 1,6-naphthyl | -CH₂-O-CH₂- | 3,4-dichlorophenyl | NH₂ |
| 24 | CH₂ | 1,5-naphthyl | -CH₂-O-CH₂- | 3,4-dichlorophenyl | NH₂ |
| 25 | CH₂ | 1,4-phenyl | CH₂ | 3,4-dichlorophenyl | NH₂ |

TABLE 6-continued

Chart of Additional Compounds 1–132

| Example | K | Ar₁ | Z | Ar₂ | R |
|---|---|---|---|---|---|
| 26 | CH₂ | 1,4-phenylene | C=O | 3,4-dichlorophenyl | NH₂ |
| 27 | CH₂ | 1,4-phenylene | SO₂ | 3,4-dichlorophenyl | NH₂ |
| 28 | CH₂ | 1,4-phenylene | S=O | 3,4-dichlorophenyl | NH₂ |
| 29 | CH₂ | 1,4-phenylene | S | 3,4-dichlorophenyl | NH₂ |
| 30 | CH₂ | 1,4-phenylene | O | 3,4-dichlorophenyl | NH₂ |

TABLE 6-continued

Chart of Additional Compounds 1–132

| Example | K | Ar$_1$ | Z | Ar$_2$ | R |
|---|---|---|---|---|---|
| 31 | CH$_2$ | 1,4-phenylene | -CH$_2$-O-CH$_2$- | 3,4-dichlorophenyl | NH$_2$ |
| 32 | CH$_2$ | 1,4-phenylene | -CH$_2$-CH=CH-CH$_2$- | 3,4-dichlorophenyl | NH$_2$ |
| 33 | CH$_2$ | 1,4-phenylene | -CH$_2$-C≡C-CH$_2$- | 3,4-dichlorophenyl | NH$_2$ |
| 34 | CH$_2$ | 1,4-phenylene | -(CH$_2$)$_4$- | 3,4-dichlorophenyl | NH$_2$ |
| 35 | CH$_2$ | 1,4-phenylene | -(CH$_2$)$_2$-C(=O)-CH$_2$- | 3,4-dichlorophenyl | NH$_2$ |

TABLE 6-continued

Chart of Additional Compounds 1–132

| Example | K | Ar₁ | Z | Ar₂ | R |
|---|---|---|---|---|---|
| 36 | CH₂ | 1,4-phenylene | -CH₂C(O)CH₂- | 3,4-dichlorophenyl | NH₂ |
| 37 | CH₂ | 1,4-phenylene | -CH₂OCH₂- | 3,4-dichlorophenyl | NH₂ |
| 38 | CH₂ | 1,4-phenylene | -CH₂CH₂O- | 3,4-dichlorophenyl | NH₂ |
| 39 | CH₂ | 1,4-phenylene | -CH₂OCH₂- | 3,4-dichlorophenyl | NH₂ |
| 40 | CH₂ | 1,4-phenylene | -C(O)NH- | 3,4-dichlorophenyl | NH₂ |

TABLE 6-continued

Chart of Additional Compounds 1-132

| Example | K | Ar$_1$ | Z | Ar$_2$ | R |
|---|---|---|---|---|---|
| 41 | CH$_2$ | p-phenylene | -C(=O)-N(CH$_3$)- | 3,4-dichlorophenyl | NH$_2$ |
| 42 | CH$_2$ | p-phenylene | -S(=O)$_2$-N(CH$_3$)- | 3,4-dichlorophenyl | NH$_2$ |
| 43 | CH$_2$ | p-phenylene | -S(=O)$_2$-N(H)- | 3,4-dichlorophenyl | NH$_2$ |
| 44 | CH$_2$ | p-phenylene | -N(H)-S(=O)$_2$- | 3,4-dichlorophenyl | NH$_2$ |
| 45 | CH$_2$ | p-phenylene | -N(CH$_3$)-S(=O)$_2$- | 3,4-dichlorophenyl | NH$_2$ |

TABLE 6-continued

Chart of Additional Compounds 1-132

| Example | K | Ar₁ | Z | Ar₂ | R |
|---|---|---|---|---|---|
| 46 | CH₂ | phenyl (1,4) | C(=O)NH | 3,4-dichlorophenyl | NH₂ |
| 47 | CH₂ | phenyl (1,4) | C(=O)N(CH₃) | 3,4-dichlorophenyl | NH₂ |
| 48 | CH₂ | phenyl (1,4) | CH₂OC(=O) | 3,4-dichlorophenyl | NH₂ |
| 49 | CH₂ | phenyl (1,4) | C(=O)OCH₂ | 3,4-dichlorophenyl | NH₂ |
| 50 | CH₂ | phenyl (1,4) | C(=O)NHCH₂ | 3,4-dichlorophenyl | NH₂ |

TABLE 6-continued

Chart of Additional Compounds 1-132

| Example | K | Ar$_1$ | Z | Ar$_2$ | R |
|---|---|---|---|---|---|
| 51 | CH$_2$ | 1,4-phenylene | -CH$_2$-N(C(=O))-CH$_2$- | 3,4-dichlorophenyl | NH$_2$ |
| 52 | CH$_2$ | 1,4-phenylene | -CH$_2$-N(C(=O))-CH$_2$- | 3,4-dichlorophenyl | NH$_2$ |
| 53 | CH$_2$ | 1,4-phenylene | -CH$_2$-NH-C(=O)-CH$_2$- | 3,4-dichlorophenyl | NH$_2$ |
| 54 | CH$_2$ | 1,4-phenylene | -CH$_2$-NH-S(=O)$_2$-CH$_2$- | 3,4-dichlorophenyl | NH$_2$ |
| 55 | CH$_2$ | 1,4-phenylene | -CH$_2$-N-S(=O)$_2$-CH$_2$- | 3,4-dichlorophenyl | NH$_2$ |

TABLE 6-continued
Chart of Additional Compounds 1–132
| Example | K | Ar₁ | Z | Ar₂ | R |
|---|---|---|---|---|---|
| 56 | 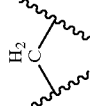 | 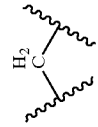 | 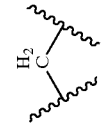 | 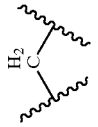 | 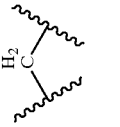 |
| 57 | 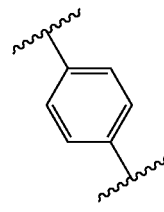 | 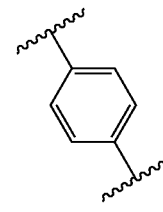 | 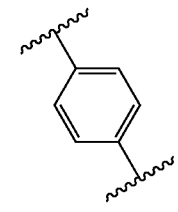 | 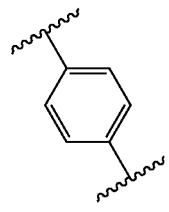 | 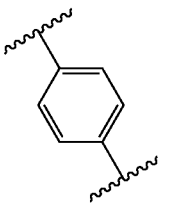 |
| 58 | 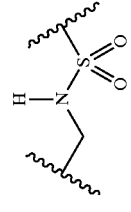 | 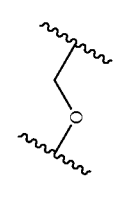 | 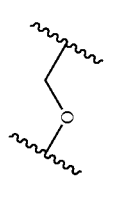 | 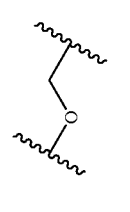 |  |
| 59 | 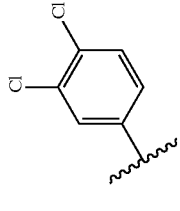 | 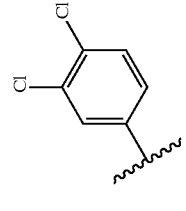 | 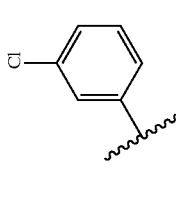 | 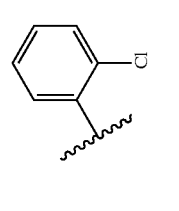 | 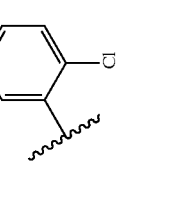 |
| 60 | 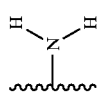 | 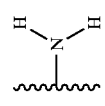 | 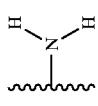 | 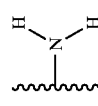 | 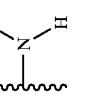 |

TABLE 6-continued

Chart of Additional Compounds 1–132

| Example | K | Ar₁ | Z | Ar₂ | R |
|---|---|---|---|---|---|
| 61 | CH₂ | p-phenylene | CH₂-O | 2,4-dichlorophenyl | NH₂ |
| 62 | CH₂ | p-phenylene | CH₂-O | 2,5-dichlorophenyl | NH₂ |
| 63 | CH₂ | p-phenylene | CH₂-O | 3,5-dichlorophenyl | NH₂ |
| 64 | CH₂ | p-phenylene | CH₂-O | 3,4-difluorophenyl | NH₂ |
| 65 | CH₂ | p-phenylene | CH₂-O | 3,4-dimethoxyphenyl | NH₂ |

TABLE 6-continued
Chart of Additional Compounds 1-132
| Example | K | $Ar_1$ | Z | $Ar_2$ | R |
|---|---|---|---|---|---|
| 66 | 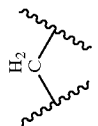 | 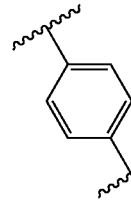 |  | 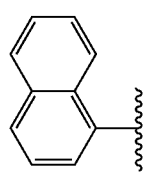 | 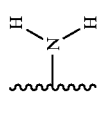 |
| 67 | 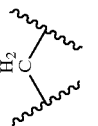 | 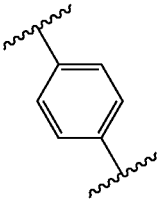 |  | 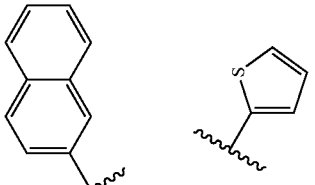 | 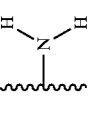 |
| 68 | 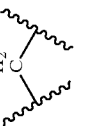 | 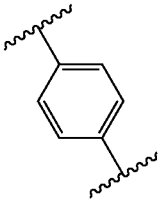 |  |  | 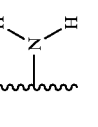 |
| 69 | 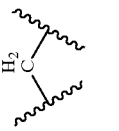 | 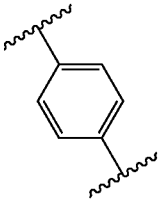 |  | 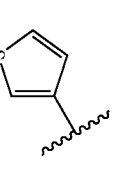 | 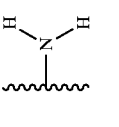 |
| 70 | 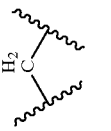 | 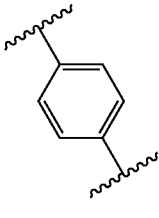 |  | 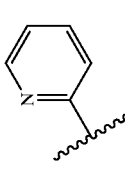 | 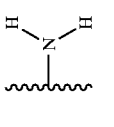 |

US 6,841,661 B2
TABLE 6-continued
Chart of Additional Compounds 1-132
| Example | K | Ar₁ | Z | Ar₂ | R |
|---|---|---|---|---|---|
| 71 | 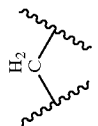 | 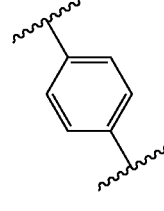 |  | 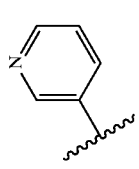 | 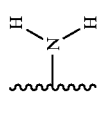 |
| 72 | 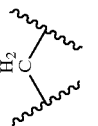 | 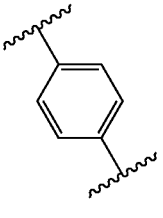 |  | 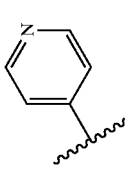 | 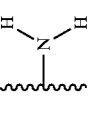 |
| 73 | 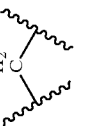 | 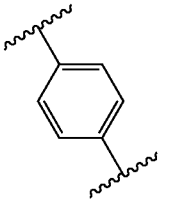 |  | 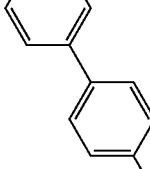 | 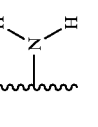 |
| 74 | 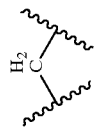 | 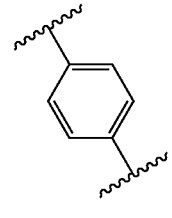 |  | 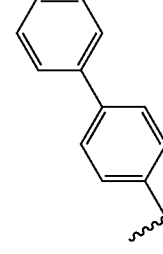 | 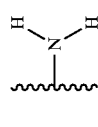 |
| 75 | 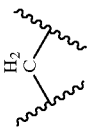 | 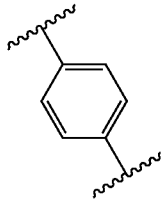 |  | 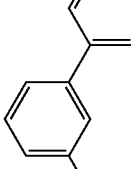 | 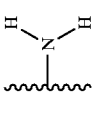 |

TABLE 6-continued

Chart of Additional Compounds 1-132

| Example | K | Ar₁ | Z | Ar₂ | R |
|---|---|---|---|---|---|
| 76 | -CH₂- | 1,4-phenylene | -CH₂CH₂-O- | 3,4-dichlorophenyl | -N(CH₃)H |
| 77 | -CH₂- | 1,4-phenylene | -CH₂CH₂-O- | 3,4-dichlorophenyl | -N(CH₃)₂ |
| 78 | -CH₂- | 1,4-phenylene | -CH₂CH₂-O- | 3,4-dichlorophenyl | -N⁺(CH₃)₃ |
| 79 | -CH₂- | 1,4-phenylene | -CH₂CH₂-O- | 3,4-dichlorophenyl | piperidin-1-yl |
| 80 | -CH₂- | 1,4-phenylene | -CH₂CH₂-O- | 3,4-dichlorophenyl | morpholin-4-yl |

TABLE 6-continued

Chart of Additional Compounds 1–132

| Example | K | Ar$_1$ | Z | Ar$_2$ | R |
|---|---|---|---|---|---|
| 81 | CH$_2$ | phenylene | -CH$_2$-O-CH$_2$- | 3,4-dichlorophenyl | 4-methylpiperazin-1-yl |
| 82 | CH$_2$ | phenylene | -CH$_2$-O-CH$_2$- | 3,4-dichlorophenyl | piperazin-1-yl |
| 83 | CH$_2$ | phenylene | -CH$_2$-O-CH$_2$- | 3,4-dichlorophenyl | pyrrolidin-1-yl |
| 84 | CH$_2$ | phenylene | -CH$_2$-O-CH$_2$- | 3,4-dichlorophenyl | -NHC(O)CH$_2$NH$_2$ |
| 85 | CH$_2$ | phenylene | -CH$_2$-O-CH$_2$- | 3,4-dichlorophenyl | -NHC(O)CH$_2$NHCH$_3$ |

TABLE 6-continued

Chart of Additional Compounds 1–132

| Example | K | Ar$_1$ | Z | Ar$_2$ | R |
|---|---|---|---|---|---|
| 86 | –CH$_2$– | 1,4-phenylene | –CH$_2$–O–CH$_2$– | 3,4-dichlorophenyl | –NH–C(O)–CH$_2$–N(CH$_3$)$_2$ |
| 87 | –CH$_2$– | 1,4-phenylene | –CH$_2$–O–CH$_2$– | 3,4-dichlorophenyl | –NH–C(O)–CH$_2$–piperidinyl |
| 88 | –CH$_2$– | 1,4-phenylene | –CH$_2$–O–CH$_2$– | 3,4-dichlorophenyl | –NH–C(O)–CH$_2$–morpholinyl |
| 89 | –CH$_2$– | 1,4-phenylene | –CH$_2$–O–CH$_2$– | 3,4-dichlorophenyl | –NH–C(O)–CH$_2$–piperazinyl |
| 90 | –CH$_2$– | 1,4-phenylene | –CH$_2$–O–CH$_2$– | 3,4-dichlorophenyl | –NH–C(O)–CH$_2$–(4-methylpiperazinyl) |

TABLE 6-continued

Chart of Additional Compounds 1–132

| Example | K | Ar$_1$ | Z | Ar$_2$ | R |
|---|---|---|---|---|---|
| 91 | CH$_2$ | 1,4-phenylene | -CH$_2$CH$_2$-O- | 3,4-dichlorophenyl | -C(O)CH$_2$N$^+$(CH$_3$)$_3$ amide |
| 92 | CH$_2$ | 1,4-phenylene | -CH$_2$CH$_2$-O- | 3,4-dichlorophenyl | alanyl amide |
| 93 | CH$_2$ | 1,4-phenylene | -CH$_2$CH$_2$-O- | 3,4-dichlorophenyl | lysyl amide |
| 94 | CH$_2$ | 1,4-phenylene | -CH$_2$CH$_2$-O- | 3,4-dichlorophenyl | arginyl amide |

TABLE 6-continued

Chart of Additional Compounds 1–132

| Example | K | Ar$_1$ | Z | Ar$_2$ | R |
|---|---|---|---|---|---|
| 95 | CH$_2$ | 1,4-phenylene | -CH$_2$-O-CH$_2$- | 3,4-dichlorophenyl | -C(O)NH-CH(CH$_2$COOH)(NH$_2$) |
| 96 | CH$_2$ | 1,4-phenylene | -CH$_2$-O-CH$_2$- | 3,4-dichlorophenyl | -C(O)NH-CH(CH$_2$CH$_2$COOH)(NH$_2$) |
| 97 | CH$_2$ | 1,4-phenylene | -CH$_2$-O-CH$_2$- | 3,4-dichlorophenyl | -C(O)NH-CH$_2$CH$_2$CH$_2$COOH |
| 98 | CH$_2$ | 1,4-phenylene | -CH$_2$-O-CH$_2$- | 3,4-dichlorophenyl | -C(O)NH-CH$_2$CH$_2$COOH |

TABLE 6-continued
Chart of Additional Compounds 1-132
| Example | K | Ar₁ | Z | Ar₂ | R |
|---|---|---|---|---|---|
| 99 | 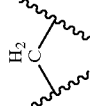 | 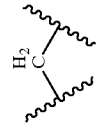 | 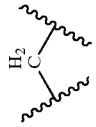 | 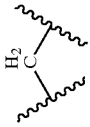 | |
| 100 | 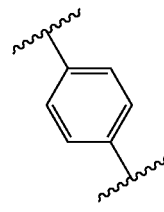 | 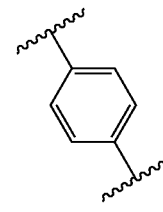 | 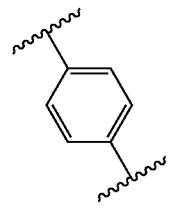 | 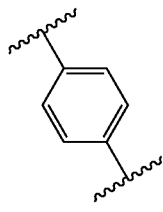 | |
| 101 | 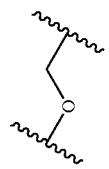 |  |  | 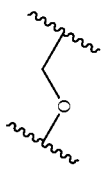 |  |
| 102 | 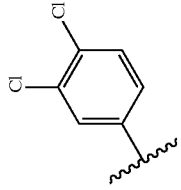 | 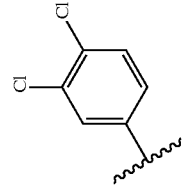 | 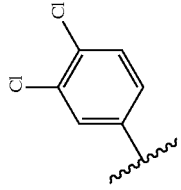 | 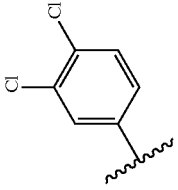 | 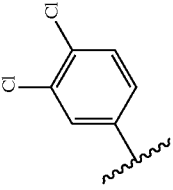 |
| 103 | 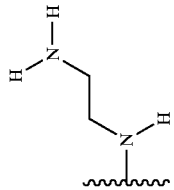 | 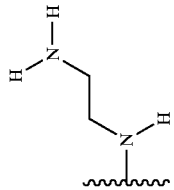 | 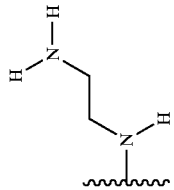 | 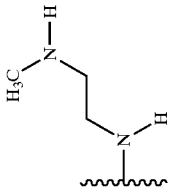 | 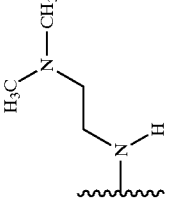 |

TABLE 6-continued

Chart of Additional Compounds 1–132

| Example | K | Ar₁ | Z | Ar₂ | R |
|---|---|---|---|---|---|
| 104 | CH₂ | 1,4-phenylene | -CH₂CH₂-O-CH₂- | 3,4-dichlorophenyl | -NH-C(=O)-CH₂CH₂-N(piperidinyl) |
| 105 | CH₂ | 1,4-phenylene | -CH₂CH₂-O-CH₂- | 3,4-dichlorophenyl | -NH-C(=O)-CH₂CH₂-N(morpholinyl) |
| 106 | CH₂ | 1,4-phenylene | -CH₂CH₂-O-CH₂- | 3,4-dichlorophenyl | -NH-C(=O)-CH₂CH₂-N(piperazinyl-NH) |
| 107 | CH₂ | 1,4-phenylene | -CH₂CH₂-O-CH₂- | 3,4-dichlorophenyl | -NH-C(=O)-CH₂CH₂-N(4-methylpiperazinyl) |

US 6,841,661 B2
TABLE 6-continued
Chart of Additional Compounds 1-132
| Example | K | Ar₁ | Z | Ar₂ | R |
|---|---|---|---|---|---|
| 108 | 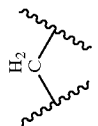 | 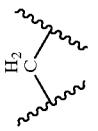 | 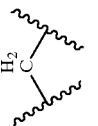 | 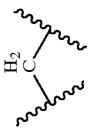 | 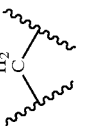 |
| 109 | 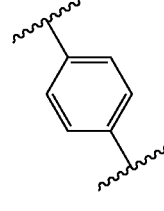 | 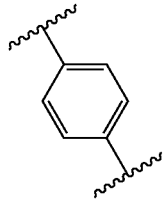 | 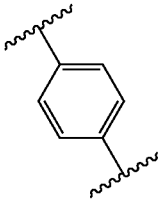 | 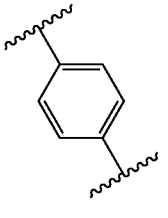 | 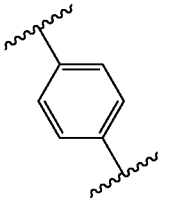 |
| 110 |  |  |  |  |  |
| 111 | 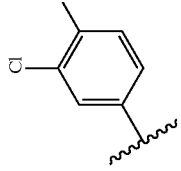 | 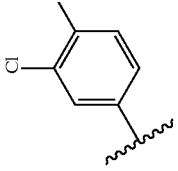 | 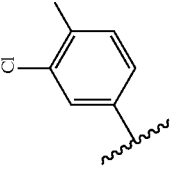 | 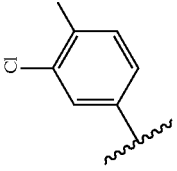 | 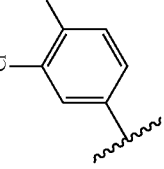 |
| 112 | 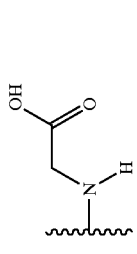 | 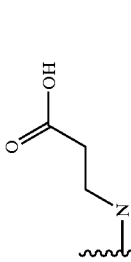 | 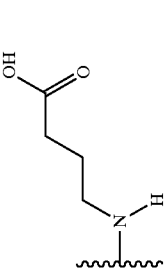 | 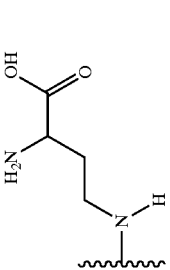 | 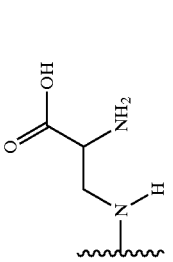 |

TABLE 6-continued

Chart of Additional Compounds 1–132

| Example | K | Ar$_1$ | Z | Ar$_2$ | R |
|---|---|---|---|---|---|
| 113 | | | | | |
| 114 | | | | | |
| 115 | | | | | |
| 116 | | | | | |
| 117 | | | | | |

TABLE 6-continued

Chart of Additional Compounds 1-132

| Example | K | Ar₁ | Z | Ar₂ | R |
|---|---|---|---|---|---|
| 118 | CH₂ | 1,4-phenylene | -CH₂-O- | 3-CN-phenyl | NH₂ |
| 119 | CH₂ | 1,4-phenylene | -CH₂-O- | 4-CN-phenyl | NH₂ |
| 120 | CH₂ | 1,4-phenylene | -CH₂-O- | 2-CN-phenyl | NH₂ |
| 121 | CH₂ | 1,4-phenylene | -CH₂-O- | 4-NH₂-phenyl | NH₂ |
| 122 | CH₂ | 1,4-phenylene | -CH₂-O- | 3-NH₂-phenyl | NH₂ |

TABLE 6-continued

Chart of Additional Compounds 1-132

| Example | K | Ar₁ | Z | Ar₂ | R |
|---|---|---|---|---|---|
| 123 | CH₂ | 1,4-phenylene | -CH₂-O-CH₂- | 2-aminophenyl | NH₂ |
| 124 | CH₂ | 1H-imidazol-2,4-diyl | -CH₂-O-CH₂- | 3,4-dichlorophenyl | NH₂ |
| 125 | CH₂ | 1H-imidazol-2,4-diyl | -CH₂-O-CH₂- | 3,4-dichlorophenyl | NH₂ |
| 126 | CH₂ | thiazol-2,5-diyl | -CH₂-O-CH₂- | 3,4-dichlorophenyl | NH₂ |
| 127 | CH₂ | thiazol-2,5-diyl | -CH₂-O-CH₂- | 3,4-dichlorophenyl | NH₂ |

TABLE 6-continued

Chart of Additional Compounds 1-132

| Example | K | Ar₁ | Z | Ar₂ | R |
|---|---|---|---|---|---|
| 128 | CH₂ | 2,4-thiazolyl | -CH₂-O-CH₂- | 3,4-dichlorophenyl | NH₂ |
| 129 | CH₂ | 2,4-thiazolyl | -CH₂-O-CH₂- | 3,4-dichlorophenyl | NH₂ |
| 130 | C(=O)O | 1,4-phenylene | -CH₂-O-CH₂- | 3,4-dichlorophenyl | NH₂ |
| 131 | C(=O)NH | 1,4-phenylene | -CH₂-O-CH₂- | 3,4-dichlorophenyl | NH₂ |
| 132 | C(=O)N(CH₃) | 1,4-phenylene | -CH₂-O-CH₂- | 3,4-dichlorophenyl | NH₂ |

Examples 133–170

Using the preparatory procedures set forth above, the following substituted compounds 133–171 of this invention are prepared and tested. In these compounds, K—Ar$_1$—Z—Ar$_2$ is (3,4-dichlorobenzyloxy)benzyl, and the polar group R is as described in the following Table 7 of compounds of the invention. The results of in vitro testing of vancomycin and teicoplanin against strains of various bacteria are also set forth.

TABLE 7

| Compound | CL4931 | CL5053 | CL5242 | CL4877 | Mean | R |
|---|---|---|---|---|---|---|
| vanco | 2048 | 2048 | 512 | 2048 | 1664.0 | |
| telco | 256 | >1024 | 256 | 0.5 | 170.8 | |
| 133 | 2 | 2 | 0.5 | 0.03 | 1.1 | 4-aminophenylmethylene |
| 134 | 2 | 4 | 1 | 0.25 | 1.8 | phenylmethylene |
| 135 | 4 | 4 | 1 | 0.06 | 2.3 | 4-aminophenylethylene |
| 136 | 4 | 4 | 1 | 0.12 | 2.3 | 4-fluorophenylmethylene |
| 137 | 4 | 4 | 1 | 0.12 | 2.3 | 3-chlorophenylmethylene |
| 138 | 8 | 4 | 1 | 0.5 | 3.4 | 4-methoxyphenylmethylene |
| 139 | 8 | 4 | 2 | 0.25 | 3.6 | 2-aminophenylmethylene |
| 140 | 4 | 8 | 2 | 0.5 | 3.6 | 2-piperidylmethylene |
| 141 | 4 | 8 | 2 | 1 | 3.8 | 4-methylphenylmethylene |
| 142 | 4 | 8 | 2 | 2 | 4.0 | 2-tetrahydrofuranylmethylene |
| 143 | 8 | 4 | 2 | 2 | 4.0 | phenylethylene |
| 144 | 4 | 8 | 2 | 2 | 4.0 | cyclopentyl |
| 145 | 8 | 8 | 1 | 0.5 | 4.4 | 2-furanomethylene |
| 146 | 8 | 8 | 1 | 0.5 | 4.4 | hydroxyethylene |
| 147 | 4 | 8 | 2 | 4 | 4.5 | methyl |
| 148 | 8 | 8 | 1 | 1 | 4.5 | n-propyl |
| 149 | 8 | 8 | 2 | 0.25 | 4.6 | 4-chlorophenylmethylene |
| 150 | 8 | 8 | 2 | 4 | 5.5 | allyl |
| 151 | 8 | 16 | 2 | 0.5 | 6.6 | phenylmethylenecarbonyl |
| 152 | 16 | 8 | 2 | 1 | 6.8 | naphthyl |
| 153 | 8 | 16 | 4 | 0.12 | 7.0 | 2-chlorophenylmethylene |
| 154 | 16 | 16 | 4 | 0.5 | 9.1 | 2-hydroxynaphthyl |
| 155 | 16 | 16 | 4 | 1 | 9.3 | 4-piperidylmethylene |
| 156 | 16 | 16 | 2 | 4 | 9.5 | 2-tetrahydropyranomethylene |
| 157 | 16 | 16 | 4 | 4 | 10.0 | cyanoethylene |
| 158 | 16 | 16 | 4 | 4 | 10.0 | 3,4-dichlorophenylmethylene |
| 159 | 16 | 16 | 4 | 4 | 10.0 | isobutylene |
| 160 | 16 | 16 | 4 | 16 | 13.0 | 3-(N-pyrrolidinylpropylene |
| 161 | 16 | 16 | 4 | 16 | 13.0 | aminopropylene |
| 162 | 16 | 16 | 4 | 16 | 13.0 | 2-(2-hydroxy)-tetrahydrofuranylmethylene |
| 163 | 16 | 32 | 4 | 2 | 13.5 | pyrrolidinyl |
| 164 | 16 | 16 | 8 | 16 | 14.0 | 3-thiophenesulfone |
| 165 | 16 | 16 | 8 | 16 | 14.0 | cyclopropanyl |
| 166 | 8 | 16 | 2 | 32 | 14.5 | 3-dimethylaminopyrrolidinyl |
| 167 | 8 | 16 | 4 | 32 | 15.0 | piperazinyl |
| 168 | 32 | 16 | 8 | 1 | 18.3 | piperidinyl |
| 169 | 32 | 32 | 8 | 1 | 18.3 | morpholinyl |
| 170 | 16 | 32 | 8 | 32 | 22.0 | 4-dimethylaminopiperidinyl |

Examples 171–189

Using the preparatory procedures set forth above, the following substituted compounds 171–189 of this invention were prepared and tested as described. In these compounds, the polar group R is amino, and K—Ar$_2$—Z—Ar$_2$ is as shown in the following Table 8 of compounds of the invention. The results of in vitro testing of vancomycin and teicoplanin against strains of various bacteria are also set forth.

TABLE 8

| | K—Ar$_2$—Z—Ar$_2$ | CL4931 | CL5053 | CL5242 | CL4877 | Mean |
|---|---|---|---|---|---|---|
| 171 | 4-(4-chlorobenzyloxybenzyl) | 4 | 8 | 1 | 16 | 7.25 |
| 172 | 4-(3-chlorobenzyloxy)benzyl | 16 | 16 | 2 | >16 | 12.5 |
| 173 | 4-(2,4-dichlorobenzyloxy)benzyl | 8 | 8 | 1 | 2 | 4.75 |
| 174 | 4-(2,5-dichlorobenzyloxy)benzyl | 16 | 16 | 8 | 16 | 14 |
| 175 | 4-(3,5-dichlorobenzyloxy)benzyl | 4 | 4 | 2 | 2 | 3 |
| 176 | 4-(2,6-dichlorobenzyloxy)benzyl | 16 | 16 | 4 | >16 | 13 |
| 177 | 4-(4-methoxycarbonylbenzyloxy)benzyl | >16 | >16 | 4 | >16 | 13 |
| 178 | 4-(4-nitrobenzyloxy)benzyl | 32 | >32 | 8 | >32 | 27 |
| 179 | 4-(4-trifluoromethylbenzyloxy)benzyl | 8 | 8 | 1 | 4 | 3.25 |
| 180 | 4-(2-trifluoromethylbenzyloxy)benzyl | 16 | 16 | 2 | 16 | 12.5 |

TABLE 8-continued

| | K—Ar$_2$—Z—Ar$_2$ | CL4931 | CL5053 | CL5242 | CL4877 | Mean |
|---|---|---|---|---|---|---|
| 181 | 4-(2-chloro-4-fluoro-benzyloxy)benzy | 16 | 32 | 4 | 32 | 21 |
| 182 | 4-(2-chloro-benzyloxy)benxyl | >16 | >16 | 4 | >16 | 13 |
| 183 | 2-chloro-4-(3,4-dichlorobenzyloxy)benzyl | 8 | 4 | 2 | 2 | 4 |
| 184 | 3-methoxy-4-(-3,4-dichlorobenzyloxy)benzyl | 4 | 4 | 2 | 8 | 4.5 |
| 185 | 2-methoxy-4(3,4-dichlorobenzyloxy)benzyl | 8 | 16 | 4 | 4 | 8 |
| 186 | 4-(3,4-dichlorophenoxy)benzyl | 8 | 8 | 2 | 8 | 6.5 |
| 187 | 4-(4-chlorophenoxycarbonyl)benzyl | 16 | 16 | 4 | 32 | 17 |
| 188 | 4-(3,4-dichlorophenoxycarbonyl)benzyl | 8 | 16 | 4 | 16 | 11 |
| 189 | 4-(3,4-dichlorophenyl)phenoxy carbonylmethyl | 32 | >32 | 32 | 32 | 32 |

Examples 190–198

Using the preparatory procedures set forth above, the following substituted compounds 190–198 of the invention are prepared and tested as described. In these compounds, K—Ar$_2$—Z—Ar$_2$ is 4(para-chlorophenyl)benzyl, and the polar groups R are as shown in the following Table 9 of compounds of the invention. The results of in vitro testing of vancomycin and teicoplanin against strains of various bacteria are also set forth.

TABLE 9

| compound | CL4931 | CL5053 | CL5242 | CL4877 | Mean | K—Ar$_2$—Z—Ar$_2$ |
|---|---|---|---|---|---|---|
| vanco | 2048 | 2048 | 512 | 2048 | 1664.0 | |
| teico | 256 | >1024 | 256 | 0.5 | 128.1 | |
| 190 | 8 | 8 | 2 | 4 | 5.5 | phenylmethylene |
| 191 | 16 | 16 | 4 | 16 | 13.0 | 2-pyridylethylene |
| 192 | 16 | 16 | 4 | 16 | 13.0 | 2-tetrahydrofuranylmethylene |
| 193 | 16 | 16 | 4 | 16 | 13.0 | 3-dimethylaminoazolinyl |
| 194 | 8 | 16 | 2 | 16 | 22.9 | n-propyl |
| 195 | 32 | 32 | 8 | 32 | 26.0 | N-pyrrolyl |
| 196 | 32 | 32 | 16 | 32 | 26.0 | morpholinyl |
| 197 | 16 | 32 | 8 | 32 | 25.0 | piperazinyl |
| 198 | 32 | 32 | 16 | 32 | 28.0 | piperidinyl |

Examples 199–215

Using the preparatory procedures set forth above, the following substituted compounds 199–215 are prepared and tested as described. In these compounds $R^1$ is 4-(3,4-dichlorophenyl)benzyl, and the polar group R is as shown in the following Table 10. The results of in vitro testing of vancomycin and teicoplanin against strains of various bacteria are also set forth.

TABLE 10

| compound | CL4931 | CL5053 | CL5242 | CL4877 | Mean | R |
|---|---|---|---|---|---|---|
| vanco | 2048 | 2048 | 512 | 2048 | 1536.0 | |
| teico | 256 | >1024 | 256 | 16 | 256.0 | |
| 199 | 4 | 4 | 0.5 | 2 | 2.6 | 2-hydroxyethylene |
| 200 | 4 | 4 | 1 | 2 | 2.8 | 4-fluorophenylmethylene |
| 201 | 4 | 4 | 1 | 4 | 3.3 | 2-tetrahydrofuranmethylene |
| 202 | 4 | 8 | 1 | 2 | 3.8 | 3-fluorocyclopentylene |
| 203 | 8 | 8 | 1 | 2 | 4.8 | phenylmethylene |
| 204 | 8 | 8 | 1 | 2 | 4.8 | 2-furanolmethylene |
| 205 | 8 | 8 | 2 | 2 | 5.0 | cyclopropylene |
| 206 | 8 | 8 | 1 | 4 | 5.3 | methyl |
| 207 | 8 | 8 | 2 | 4 | 5.5 | ethyl |
| 208 | 8 | 4 | 2 | 8 | 5.5 | (2-thiophene)methylene |
| 209 | 8 | 8 | 2 | 4 | 5.5 | 2-chlorophenylmethylene |
| 210 | 16 | 8 | 2 | 4 | 7.5 | 4-aminophenylmethylene |
| 211 | 16 | 8 | 4 | 4 | 8.0 | 3-chlorophenylmethylene |
| 212 | 16 | 8 | 4 | 4 | 8.0 | 2-aminophenylmethylene |
| 213 | 16 | 16 | 4 | 8 | 11.0 | 2-pyridylmethylene |
| 214 | 16 | 16 | 4 | 8 | 11.0 | 4-pyridylmethylene |
| 215 | 32 | 32 | 4 | 32 | 25.0 | piperazino |

What is claimed is:

1. A vancomycin analog whose glucose C-6 position is modified to bear a polar substituent other than a naturally occurring hydroxyl group and whose vancosamine is substituted at the amine nitrogen with a substituent having at least a first aryl moiety and second aryl moiety joined together by a first flexible linker moiety that is not a single bond, directly joining the first aryl moiety and the second aryl moiety or a pharmaceutically acceptable salt thereof.

2. The analog of claim 1 in which a second flexible linker moiety, the same as or different from the first, joins the amine nitrogen of the vancosamine and the first aryl moiety of the substituent.

3. The analog of claim 1 in which the substituent falls within the scope of the formula K—Ar$_1$—Z—Ar$_2$, in which Ar$_1$ and Ar$_2$ represent a first aryl moiety and a second aryl moiety, respectively, and K and Z represent a second flexible linker moiety and a first flexible linker moiety, respectively, provided that Z is not a single bond joining Ar$_1$ and Ar$_2$.

4. The analog of claim 1 in which the substituent comprises a benzyloxybenzyl group.

5. The analog of claim 4 in which said benzyloxybenzyl group is further substituted by one or more halide groups.

6. The analog of claim 1 in which the polar substituent is a free amine.

7. The analog of claim 1 in which the polar substituent is a substituted amine that provides for a primary or secondary amine at a distal position.

8. The analog of claim 1 in which the polar substituent is charged at or about physiological pH.

9. The analog of claim 3 having the Formula I, below:

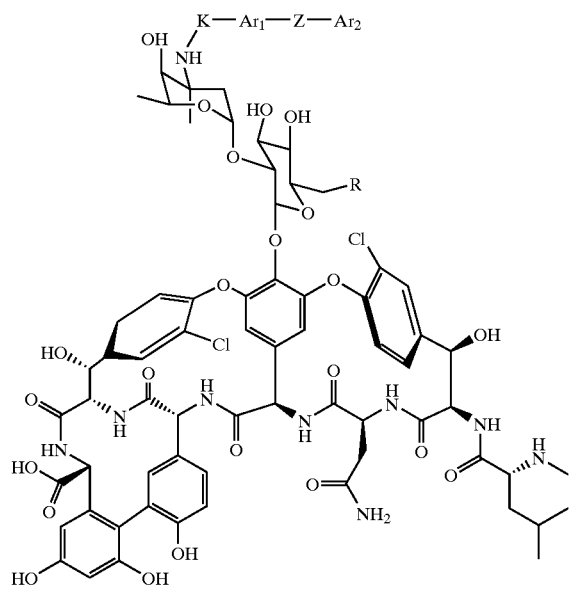

I in which the group K—Ar$_1$—Z—Ar$_2$ is as described above and R is a group which has the formula:

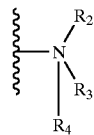

in which the groups R$_3$ and R$_4$ may be the same or different and selected from the group consisting of H, alkyl, aryl, heterocyclic, aralkyl, heterocyclicalkyl, alkylcarbonyl, arylcarbonyl, heterocycliccarbonyl, aminocarbonyl, substituted arninocarbonyl, substituted oxycarbonyl, alkylsulfonyl, arylsulfonyl, heterocyclicsulfonyl, aminosulfonyl, substituted aminosulfonyl, amidino, or substituted amidino, said alkyl, aryl, heterocyclic, arylalkyl, heterocyclicalkyl, alkylcarbonyl, arylcarbonyl, or heterocycliccarbonyl being optionally substituted with 1–3 groups of R$_1$; and wherein R$_3$ and R$_4$ may be linked to one another or to one or both of the others by one or more covalent bonds to form one or more aryl or heterocyclic rings of 3–20 members, optionally comprised of C, N, O, or S, provided that Z is not a single bond directly joining Ar$_1$ and Ar$_2$.

10. The analog of claim 9 in which the group K is a CH$_2$.

11. The analog of claim 10 in which the group Z is an OCH$_2$.

12. The analog of claim 11 in which Ar$_1$ is phenylene.

13. The analog of claim 12 in which Ar$_2$ is dichlorophenyl.

14. The analog of claim 13, which is:

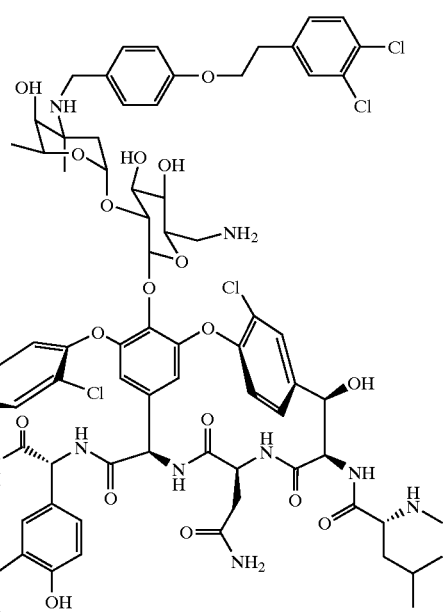

15. The analog of claim 1, which is: Glucos-6-amino-N-4-(3,4-dichlorobenzyloxy)benzyl-vancosamino-vancomycin, N-(3-Pyridyl)methyl-glucos-6-amino-N-4-(3,4-dichlorobenzyloxy)benzyl-vancosamino-vancomycin, N-Glycyl-glucos-6-amino-N-4-(3,4-dichlorobenzyloxy)benzyl-vancosamino-vancomycin, N-L-Alanyl-glucos-6-amino-N-4-(3,4-dichlorobenzyloxy)benzyl-vancosamino-vancomycin, or N-D-Alanyl-glucos-6-amino-N-4-(3,4-dichlorobenzyloxy)benzyl-vancosamino-vancomycin, or pharmaceutically acceptable salts thereof.

16. The analog of claim 1, which is: N-L-Prolyl-glucos-6-amino-N-4-(3,4-dichlorobenzyloxy)benzyl-vancosaminovancomycin, N-8-Alanyl-glucos-6-amino-N-4(3,4-dichlorobenzyloxy)benzyl-vancosamino-vancomycin, N-L-Lysyl-glucos-6-amino-N-4-(3,4-dichlorobenzyloxy)benzyl-vancosamino-vancomycin, N-L-(3-thiazolyl)alanyl-glucos-6-amino-N-4(3,4-dichlorobenzyloxy)benzyl-vancosamino vancomycin, N-L-(2-thienyl)alanyl-glucos-6-amino-N-4-(3,4-dichlorobenzyloxy)benzyl-vancosamino-vancomycin, N-L-Asparagyl-glucos-6-amino-N-4-(3,4-dichlorobenzyloxy)benzyl-vancosamino-vancomycin, or N-D-(3-pyridyl)alanyl-glucos-6-amino-N-4-(3,4-dichloro benzyloxy)benzyl-vancosamino-vancomycin or pharmaceutically acceptable salts thereof.

17. An analog of claim 3 wherein K and Z are selected from the group consisting of carbonyl, sulfonyl, $(C_{1-6})$alkylene, $(C_{1-6})$alkyleneoxy, oxy$(C_{1-6})$alkylene, $(C_{1-6})$alkyleneamino, amino$(C_{1-6})$alkylene, $(C_{1-3})$alkyleneoxy-$(C_{1-3})$alkylene, $(C_{1-6})$alkylenethio, thio$(C_{1-6})$alkylene, $(C_{1-6})$alkylenecarbonyl, aminocarbonyl or carbonylamino, $(C_{1-6})$alkyleneaminocarbonyl, aminocarbonyl$(C_{1-6})$alkylene, oxy, oxycarbonyl or carbonyloxy, $(C_{1-6})$alkyleneoxycarbonyl, oxycarbonyl$(C_{1-6})$alkylene, aminosulfonyl, or sulfonylamino.

18. An analog of claim 3 wherein $Ar_1$ and $Ar_2$ may be the same or different are selected from the group consisting of aromatic or heterocyclic groups, each optionally monosubstituted, disubstituted, or trisubstituted with $R_1$; wherein $R_1$ can be halo; $R_2$; CN; $NO_2$; $CF_3$; $OCH_xF_{(3-x)}$ $(x=0-3)$; $NHSO_2R_2$; $OR_2$; $SR_2$; $N(R_2)_2$; $N^+(R_2)_3$; $C(O)N(R_2)_2$; $SO_2N(R_2)_2$; heterocyclic; $CO_2R_2$; $C(O)R_2$; $OC(O)R_2$; $NR_2C(O)R_2$; or $NHC(O)R_2$; and wherein $R_2$ independently (where more than one $R_2$ is present) represents H, aryl, straight or branched $(C_{1-6})$alkyl, arylalkyl, heterocyclic, heterocyclic$(C_1-C_6)$alkyl, aroyl, alkanoyl, alkanoyloxy, alkanoylamido, alkylsulfonyl, arylsulfonyl; and when two $R_2$ groups are present, they may optionally be linked by one or more covalent bonds to form one or more rings, which may be aromatic, aliphatic, or heterocyclic.

19. An analog according to claim 1, wherein the $C_6$ polar substituent is a group R which has the formula:

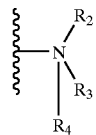

in which the groups $R_3$ and $R_4$ may be the same or different and selected from the group consisting of H, alkyl, aryl, heterocyclic, aralkyl, heterocyclicalkyl, alkylcarbonyl, arylcarbonyl, heterocycliccarbonyl, aminocarbonyl, substituted arninocarbonyl, substituted oxycarbonyl, alkylsulfonyl, arylsulfonyl, heterocyclicsulfonyl, aminosulfonyl, substituted aminosulfonyl, amidino, or substituted amidino, said alkyl, aryl, heterocyclic, arylalkyl, heterocyclicalkyl, alkylcarbonyl, arylcarbonyl, or heterocycliccarbonyl being optionally substituted with 1–3 groups of $R_1$; and wherein $R_3$ and $R_4$ may be linked to one another or to one or both of the others by one or more covalent bonds to form one or more aryl or heterocyclic rings of 3–20 members, optionally comprised of C, N, O, or S.

* * * * *